(12) United States Patent
Levi et al.

(10) Patent No.: US 9,679,672 B2
(45) Date of Patent: Jun. 13, 2017

(54) LOW BAND GAP CONJUGATED POLYMERIC COMPOSITIONS AND APPLICATIONS THEREOF

(71) Applicant: WAKE FOREST UNIVERSITY, Winston, Salem, NC (US)

(72) Inventors: Nicole Levi, Winston-Salem, NC (US); David L. Carroll, Winston-Salem, NC (US); Christopher MacNeill, Winston-Salem, NC (US); Elizabeth Graham, Mount Pleasant, SC (US)

(73) Assignee: Wake Forest University, Winston-Salem, NC (US)

( * ) Notice: Subject to any disclaimer, the term of this patent is extended or adjusted under 35 U.S.C. 154(b) by 225 days.

(21) Appl. No.: 14/394,198

(22) PCT Filed: Apr. 12, 2013

(86) PCT No.: PCT/US2013/036451
§ 371 (c)(1),
(2) Date: Oct. 13, 2014

(87) PCT Pub. No.: WO2013/155463
PCT Pub. Date: Oct. 17, 2013

(65) Prior Publication Data
US 2015/0069302 A1    Mar. 12, 2015

Related U.S. Application Data

(60) Provisional application No. 61/623,886, filed on Apr. 13, 2012.

(51) Int. Cl.
*H01B 1/12*    (2006.01)
*H01L 51/00*   (2006.01)
(Continued)

(52) U.S. Cl.
CPC .......... *H01B 1/127* (2013.01); *A61K 41/0052* (2013.01); *A61K 47/48192* (2013.01);
(Continued)

(58) Field of Classification Search
None
See application file for complete search history.

(56) References Cited

U.S. PATENT DOCUMENTS

| | | | |
|---|---|---|---|
| 2006/0258802 A1 | 11/2006 | Janietz et al. | |
| 2008/0121281 A1* | 5/2008 | Gaudiana | C08G 61/123 136/263 |
| 2008/0265215 A1* | 10/2008 | Wessling | B82Y 30/00 252/500 |

FOREIGN PATENT DOCUMENTS

| AT | WO 2012016298 A1 * | 2/2012 | ............... C09D 5/24 |
|---|---|---|---|
| CN | 102698268 A | 10/2012 | |

(Continued)

OTHER PUBLICATIONS

English text machine translation of FR 2902007 A1, accessed online from Espacenet, a copy of which is attached to the case file as a PDF, pp. 1-20.*

(Continued)

*Primary Examiner* — Harold Pyon
*Assistant Examiner* — Katie L Hammer
(74) *Attorney, Agent, or Firm* — J. Clinton Wimbish; Smith Moore Leatherwood LLP

(57) ABSTRACT

In one aspect, electrically conductive conjugated polymeric compositions are described herein demonstrating compatibility with aqueous solvents and/or phases. The ability to provide aqueous compatible compositions from previously water insoluble conjugated polymeric systems, in some embodiments, can facilitate use of such systems in a variety of aqueous applications, including biological applications.

19 Claims, 21 Drawing Sheets

(51) Int. Cl.
*C08F 126/06* (2006.01)
*C08F 28/06* (2006.01)
*A61K 41/00* (2006.01)
*A61K 47/48* (2006.01)
*C08G 61/12* (2006.01)
*C08L 65/00* (2006.01)
*A61N 5/06* (2006.01)
*A61N 7/00* (2006.01)

(52) U.S. Cl.
CPC .............. *C08F 28/06* (2013.01); *C08F 126/06* (2013.01); *C08G 61/123* (2013.01); *C08G 61/126* (2013.01); *C08L 65/00* (2013.01); *H01L 51/0043* (2013.01); *A61N 5/062* (2013.01); *A61N 7/00* (2013.01); *A61N 2005/0659* (2013.01); *C08G 2261/124* (2013.01); *C08G 2261/1412* (2013.01); *C08G 2261/323* (2013.01); *C08G 2261/3229* (2013.01); *C08G 2261/3243* (2013.01); *C08G 2261/3245* (2013.01); *C08G 2261/3246* (2013.01); *C08G 2261/3247* (2013.01); *C08G 2261/414* (2013.01); *C08G 2261/90* (2013.01)

(56) References Cited

FOREIGN PATENT DOCUMENTS

| | | | |
|---|---|---|---|
| FR | 2902007 A1 * | 12/2007 | ........... A61K 9/0019 |
| WO | 94/04614 | 3/1994 | |

OTHER PUBLICATIONS

Henry J. Snaith, et al., "Photovoltaic devices fabricated from an aqueous dispersion of polyfluorene nanopadicles using an electroplating method", Synthetic Metals 147, (2004), pp. 105-109.

Zhuang Liu et al., "Electroconductive polymer nanomaterial and its application for treating cancer", Chemical Abstracts Service, Oct. 8, 2012, 1 page.

Jaemoon Yang et al., "Convertible Organic Nanoparticles for Near-Infrared Photothermal Ablation of Cancer Cells", Angewandte Chemie International Edition, vol. 50, No. 2, Jan. 10, 2011, pp. 441-444.

* cited by examiner

X = O, N, S, or Se    R, $R_1$, $R_2$ and $R_3$ = H, alkyl, alkenyl, aryl, heteroaryl, O-alkyl, O-alkenyl, or O-aryl X = O, N, S, or Se    R, R₁ and R₂ = H, alkyl, alkenyl, aryl, heteroaryl, O-alkyl, O-alkenyl, or O-aryl (a)
 (b)
 (c)
 (d)

LOW BAND GAP CONJUGATED POLYMERIC COMPOSITIONS AND APPLICATIONS THEREOF

RELATED APPLICATION DATA

The present application is a national stage application under 35 U.S.C. §371 of International Application No. PCT/US2013/036451, filed Apr. 12, 2013, which claims priority pursuant to 35 U.S.C. §119(e) to United States Provisional Patent Application Serial Number 61/623,886 filed Apr. 13, 2012 which is hereby incorporated by reference in its entirety.

FIELD

The present invention relates to low band gap conjugated polymeric compositions and, in particular, to aqueous mixtures comprising low band gap conjugated polymeric compositions.

BACKGROUND

Electrically conductive conjugated polymers show excellent charge transport properties making them suitable materials for nanostructured devices. Many conjugated polymers have been fabricated into devices such as organic photovoltaics, light emitting diodes and field-effect transistors. The low band gap nature of some conjugated polymers allows them to be very efficient electron donors due to how well they absorb visible and NIR light, generate excitons and subsequently transfer the charge to an electron acceptor, such as a $C_{60}$ derivative.

Conjugated polymers are readily soluble in organic solvents and concomitantly insoluble in aqueous media. Such insolubility has limited application of conjugated polymer systems to a variety of applications requiring compatibility with aqueous solvents and/or phases.

SUMMARY

In one aspect, electrically conductive conjugated polymeric compositions are described herein demonstrating compatibility with aqueous solvents and/or phases. The ability to provide aqueous compatible compositions from previously water insoluble conjugated polymeric systems, in some embodiments, can facilitate use of such systems in a variety of aqueous applications, including biological applications.

Compositions described herein comprise water insoluble conjugated polymers in aqueous media. In some embodiments, aqueous solutions of water insoluble conjugated polymers are described herein. A solution, in some embodiments, comprises an aqueous solvent and a solute comprising at least one water insoluble conjugated polymer, wherein the water insoluble conjugated polymer is not modified with one or more chemical species operable to increase the aqueous solubility or dispersibility of the conjugated polymer. Alternatively, in other embodiments, the water insoluble conjugated polymer is at least partially encapsulated by a dispersing agent. In addition, as described further herein, the water insoluble conjugated polymer of a solution, in some embodiments, is a sonicated water insoluble conjugated polymer.

In another aspect, colloidal compositions are described herein. A colloidal composition, in some embodiments, comprises an aqueous or aqueous-based continuous phase and a dispersed phase comprising at least one water insoluble conjugated polymer, wherein the water insoluble conjugated polymer is not modified with one or more chemical species operable to increase the aqueous solubility or dispersibility of the conjugated polymer. Alternatively, in other embodiments, the water insoluble conjugated polymer is at least partially encapsulated by a dispersing agent. In some embodiments, the water insoluble conjugated polymer of a colloidal composition described herein is a sonicated water insoluble conjugated polymer.

A colloidal composition, in another embodiment, comprises an aqueous or aqueous-based continuous phase and a dispersed phase comprising at least one conjugated polymer, wherein the colloidal composition demonstrates an increase in temperature when irradiated with electromagnetic radiation of wavelength matching or substantially matching the absorption maximum of the conjugated polymer, the increase in temperature being at least 10 times (10×) greater than an increase in temperature of water irradiated under conditions matching the conjugated polymer irradiation wherein the conjugated polymer is present in an amount ranging from about 1 ng/ml to about 100 mg/ml.

In some embodiments, a composition described herein comprises an aqueous medium and particles of at least one water insoluble conjugated copolymer in the aqueous medium, the water insoluble conjugated copolymer having a donor-acceptor architecture comprising a donor monomeric species (D) and an acceptor monomeric species (A). In some embodiments, the particles of the water insoluble conjugated copolymer are dispersed in the aqueous medium to provide a colloid. Further, in some embodiments, the particles are not modified with one or more chemical species operable to increase the aqueous solubility of the copolymer in excess of 0.001 percent. Alternatively, in other embodiments, the particles of the water insoluble conjugated copolymer are at least partially encapsulated by a dispersing agent.

In another aspect, methods of making aqueous solutions of water insoluble conjugated polymers are described herein. In some embodiments, a method of making an aqueous solution comprises providing an organic solution phase comprising a water insoluble conjugated polymer in an organic solvent, providing an aqueous phase in contact with the organic solution phase and solubilizing at least some of the water insoluble polymer in the aqueous phase by sonication and evaporation of the organic solvent to provide the aqueous solution, wherein the water insoluble conjugated polymer is not modified with one or more chemical species operable to increase the aqueous solubility or dispersibility of the conjugated polymer.

A method of making an aqueous solution, in another embodiment, comprises providing an organic phase comprising a solution of a water insoluble conjugated polymer in an organic solvent, providing an aqueous phase in contact with the organic phase and solubilizing at least some of the water insoluble conjugated polymer in the aqueous phase by sonicating the organic solvent to provide the aqueous solution, wherein the aqueous phase comprises at least one dispersing agent and the water insoluble conjugated polymer is at least partially encapsulated by the dispersing agent.

In another aspect, methods of making colloidal compositions are described herein. A method of making a colloidal composition, in some embodiments, comprises providing an organic solution phase comprising a water insoluble conjugated polymer in an organic solvent, providing an aqueous phase in contact with the organic solution phase and dispersing at least some of the water insoluble conjugated polymer in the aqueous phase by sonication and evaporation of the organic solvent to provide the colloidal composition, wherein the water insoluble conjugated polymer is not modified with one or more chemical species operable to increase the aqueous or solubility or dispersibility of the conjugated polymer.

A method of making a colloidal composition, in another embodiment, comprises providing an organic phase comprising a solution of a water insoluble conjugated polymer in an organic solvent, providing an aqueous phase in contact with the organic phase and dispersing at least some of the water insoluble conjugated polymer in the aqueous phase by sonication and evaporation of the organic solvent to provide the colloidal composition, wherein the aqueous phase comprises at least one dispersing agent and the water insoluble conjugated polymer is at least partially encapsulated by the dispersing agent.

In another aspect, methods of treating diseased tissue are described herein. In some embodiments, a method of treating diseased tissue comprises providing a solution comprising an aqueous or aqueous-based solvent and a solute comprising at least one water insoluble conjugated polymer and disposing the solution in diseased tissue, wherein the water insoluble conjugated polymer is not modified with one or more chemical species operable to increase the aqueous solubility or dispersibility of the conjugated polymer. Alternatively, in some embodiments, the water insoluble conjugated polymer is at least partially encapsulated by a dispersing agent. Thermal energy is provided to the diseased tissue by irradiating the conjugated polymer. In some embodiments, hyperthermia and/or other cellular death mechanisms are induced in the diseased tissue from the induced heating resulting in ablation or killing of cells of the diseased tissue.

In some embodiments, a method of treating diseased tissue comprises providing a colloidal composition comprising an aqueous or aqueous-based continuous phase and a dispersed phase comprising at least one water insoluble conjugated polymer and disposing the colloidal composition in diseased tissue, wherein the water insoluble conjugated polymer is not modified with one or more chemical species operable to increase the aqueous solubility or dispersibility of the conjugated polymer. Alternatively, in some embodiments, the water insoluble conjugated polymer is at least partially encapsulated by a dispersing agent. Thermal energy is provided to the diseased tissue by irradiating the conjugated polymer. In some embodiments, hyperthermia and/or other cellular death mechanisms are induced in the diseased tissue from the induced heating resulting in ablation or killing of cells of the diseased tissue.

In another aspect, disease treatment systems are described herein. In some embodiments, a disease treatment system comprises a source of radiation or ultrasound and a composition including an aqueous medium and particles of at least one water insoluble conjugated copolymer in the aqueous medium. In some embodiments, the water insoluble conjugated copolymer has a donor-acceptor architecture comprising a donor monomeric species (D) and an acceptor monomeric species (A). In addition, in some embodiments, the radiation provided by the source of radiation or ultrasound at least partially falls within the absorption profile of the water insoluble conjugated polymer.

These and other embodiments are described in greater detail in the detailed description which follows.

DETAILED DESCRIPTION

Figure 1:
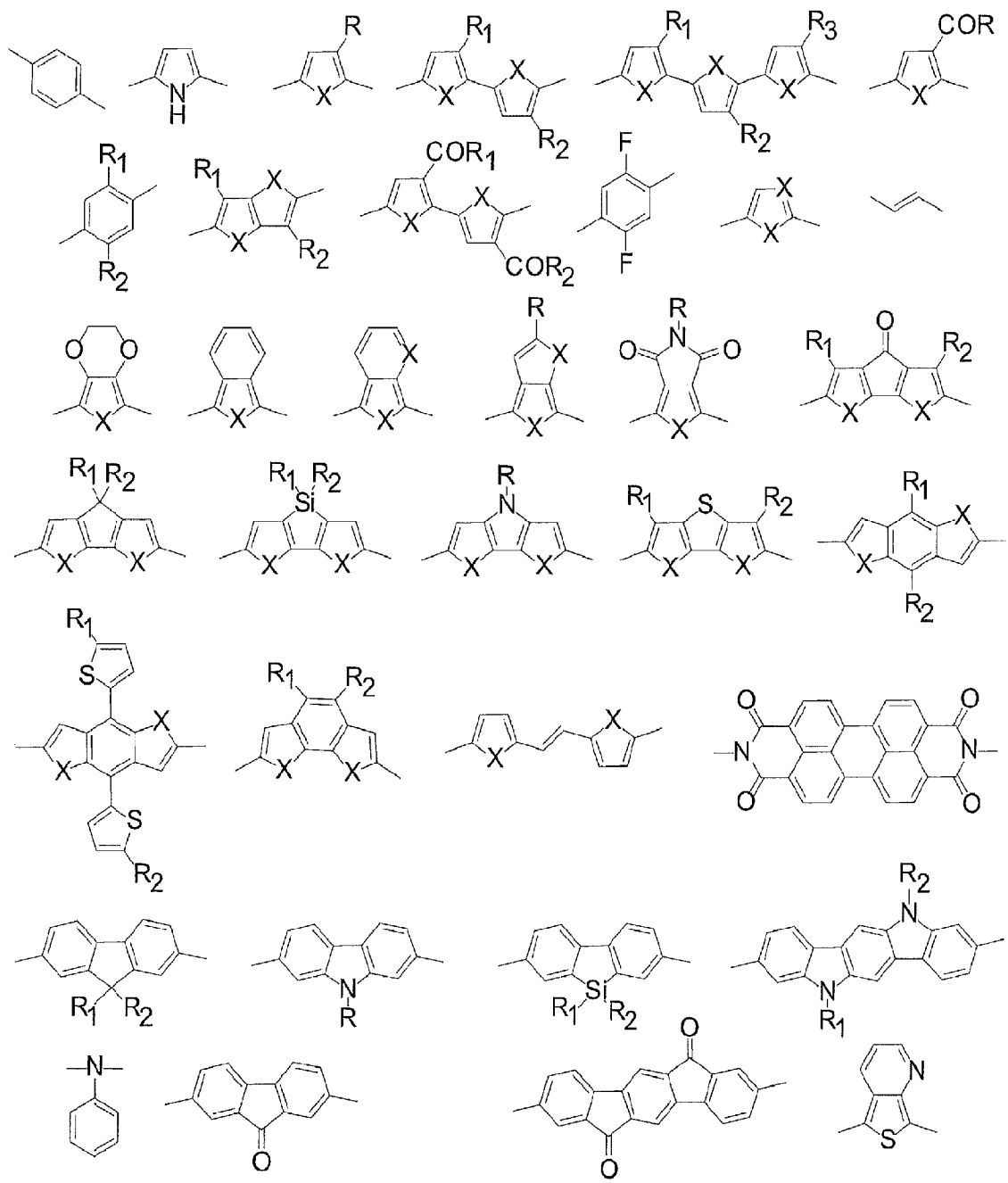
FIG. 1 illustrates monomeric species of a water insoluble conjugated polymer according to some embodiments described herein.

Embodiments described herein can be understood more readily by reference to the following detailed description and examples and their previous and following descriptions. Elements, apparatus and methods described herein, however, are not limited to the specific embodiments present in the detailed description and examples. It should be recognized that these embodiments are merely illustrative of principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

Further, when the phrase "up to" is used in connection with an amount, it is to be understood that the amount is at least a detectable amount. For example, a material present in an amount "up to" a specified amount can be present from a detectable amount and up to and including the specified amount.

In one aspect, electrically conductive conjugated polymeric compositions are described herein demonstrating compatibility with aqueous solvents and/or phases. The ability to provide aqueous compatible compositions from previously water insoluble conjugated polymeric systems, in some embodiments, can facilitate or permit use of such systems in a variety of applications, including biological applications. Compositions described herein, for example, comprise conjugated polymers in aqueous media.

I. Aqueous Solutions of Water Insoluble Conjugated Polymers

In some embodiments, aqueous solutions of water insoluble conjugated polymers are described herein. A solution, in some embodiments, comprises an aqueous solvent and a solute comprising at least one water insoluble conjugated polymer, wherein the water insoluble conjugated polymer is not modified with one or more chemical species operable to increase the solubility of the conjugated polymer.

Alternatively, in other embodiments, a solution comprises an aqueous solvent and a solute comprising at least one water insoluble conjugated polymer, wherein the water insoluble conjugated polymer is at least partially encapsulated by a dispersing agent. The dispersing agent, in some embodiments, comprises an amphiphilic chemical species. Moreover, in some embodiments, a dispersing agent is non-covalently associated with the water insoluble conjugated polymer. For example, in some embodiments, a dispersing agent is associated with the water insoluble conjugated polymer through one or more of hydrogen bonding, electrostatic bonding, ionic bonding, dipole-dipole forces, and van der Waals interactions. In other embodiments, the dispersing agent is associated with the water insoluble conjugated polymer through one or more covalent bonds. In addition, in some embodiments, a dispersing agent described herein further comprises a light emitting species.

Turning now to specific components, solutions described herein comprise an aqueous solvent. In some embodiments, an aqueous solvent is water. Further, in some embodiments, an aqueous solvent comprises water and one or more other chemical species. In some embodiments wherein the aqueous solvent comprises chemical species in addition to water, the chemical species are not operable to increase or substantially increase the aqueous solubility or dispersibility of the water insoluble conjugated polymer. Alternatively, the aqueous solvent comprises chemical species operable to increase the aqueous solubility or dispersibility of the water insoluble conjugated polymer.

Any suitable water insoluble electrically conductive conjugated polymer not inconsistent with the objectives of the present invention can be used as a solute in aqueous solutions described herein. Water insoluble conjugated polymers can demonstrate a band gap ranging from about 1.1 eV to about 1.8 eV. In having a band gap ranging from about 1.1 eV to about 1.8 eV, conjugated polymers of solutions described herein are operable to absorb electromagnetic radiation in the near infrared region (NIR) of the electromagnetic spectrum.

In some embodiments, a water insoluble conjugated polymer is a homopolymer. For example, a homopolymer can be constructed of a donor monomeric species (D), wherein D is a monocyclic, bicyclic or polycyclic arylene or monocyclic, bicyclic or polycyclic heteroarylene. The arylene structures, in some embodiments, can be fused or linked. A water insoluble conjugated homopolymer, in some embodiments, is constructed of a monomer selected from the group consisting of aniline, pyrrole, thiophene, 3-substituted thiophene, bithiophene, terthiophene, selenophene, 3-substituted selenophene, isothianaphthene, p-phenylenevinylene, ethylenedioxythiophene, propylenedioxythiophene, 2,7-fluorene, substituted 2,7-fluorene, 2,7-carbazole, substituted 2,7-carbazole, thieno[3,2-b]thiophene, thieno[3,4-b]thiophene, dithienothiophene, cyclopenta[2,1-b:3,4-b']dithiophene, substituted cyclopenta[2,1-b:3,4-b']dithiophene, dithieno[3,2-b:2',3'-d]silole, benzo[1,2-b:4,5-b']dithiophene, benzo[1,2-b;3,4-b']dithiophene, indolo[3,2-b]carbazoles, dithieno[3,2-b:2',3'-d]pyrrole, diketopyrrolopyrrole, pentacene, heptacene and perylenediimine. Some suitable donor monomeric species are further illustrated in FIG. 1. In the structures of FIG. 1, X can be O, N, S or Se. In some embodiments comprising more than one X, each X can independently be O, N, S or Se. In addition, R, $R_1$, $R_2$ and $R_3$ can independently be selected from the group consisting of hydrogen, alkyl, alkenyl, aryl, heteroaryl, O-alkyl, O-alkenyl, and O-aryl. An alkyl, alkenyl, aryl, heteroaryl, O-alkyl, O-alkenyl, or O-aryl group, in some embodiments, comprises between 1 and 30 carbon atoms or between 1 and 15 carbon atoms.

Figure 2:
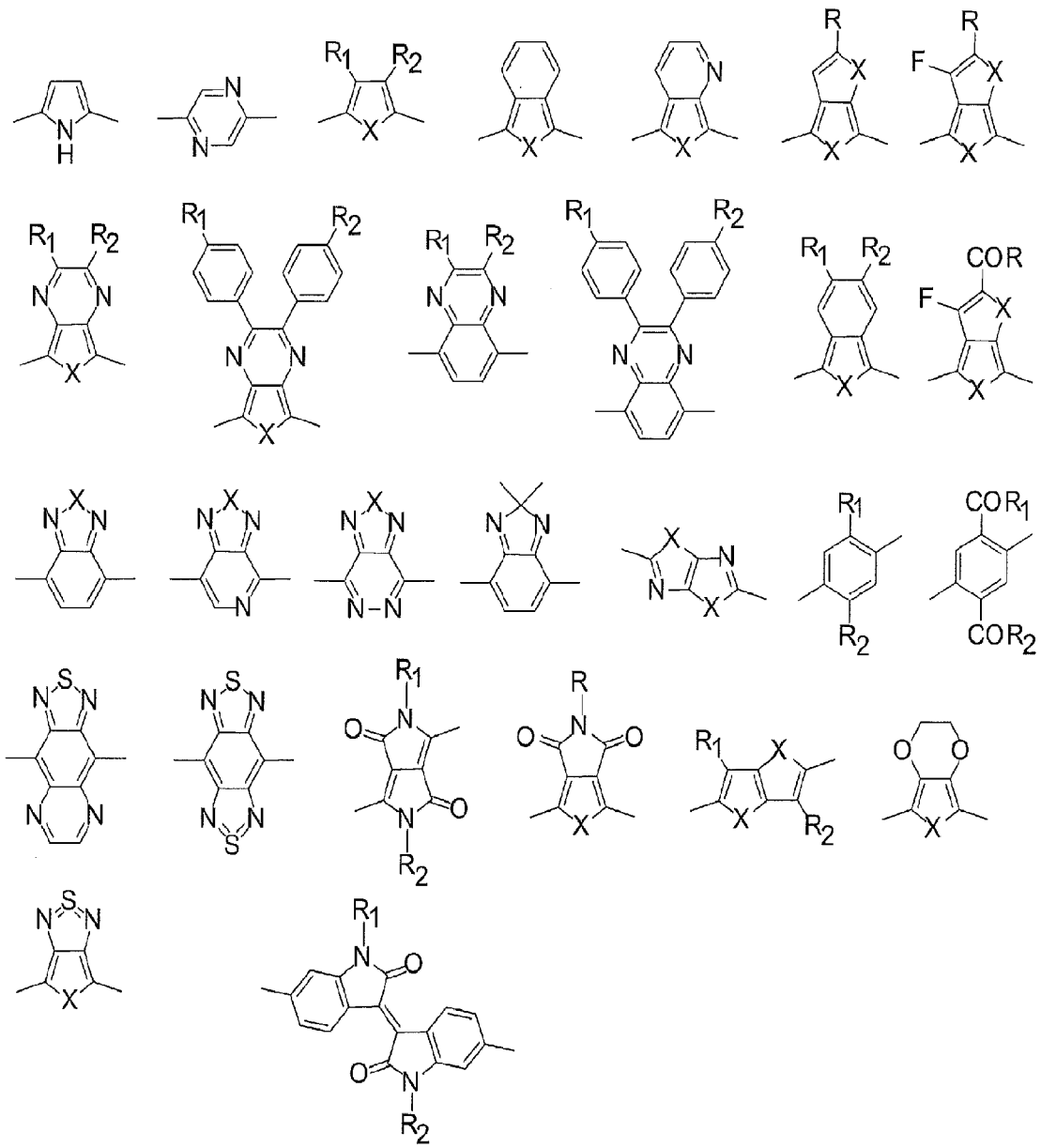
FIG. 2 illustrates monomeric species of a water insoluble conjugated polymer according to some embodiments described herein.

Additionally, a water insoluble conjugated homopolymer can be constructed of an acceptor monomeric species (A), wherein A is a monocyclic, bicyclic or polycyclic arylene or monocyclic, bicyclic or polycyclic heteroarylene. The arylene structures, in some embodiments, can be fused or linked. A water insoluble conjugated homopolymer, in some embodiments, is constructed of a monomer selected from the group consisting of pyrrole, aniline, thiophene, ethlyenedioxythiophene, p-phenylenevinylene, benzothiadiazole, pydridinethiadiazole, pyridineselenadiazole, benzoxadiazole, benzoselenadiazole, thieno[3,4-b]pyrazine, thieno[3,4-b]thiophene, thieno[3,2-b]thiophene, [1,2,5]thiadiazolo[3,4-g]quinoxaline, pyrazino[2,3-g]quinoxaline, thienopyrrolidinone and isothianaphthene. Some suitable acceptor monomeric species are further illustrated in FIG. 2. In the structures of FIG. 2, X can be O, N, S or Se. In some embodiments comprising more than one X, each X can independently be O, N, S or Se. In addition, R, $R^1$ and $R^2$ can independently be selected from the group consisting of hydrogen, alkyl, alkenyl, aryl, heteroaryl, O-alkyl, O-alkenyl, and O-aryl. An alkyl, alkenyl, aryl, heteroaryl, O-alkyl, O-alkenyl, or O-aryl group, in some embodiments, comprises between 1 and 30 carbon atoms or between 1 and 15 carbon atoms.

Alternatively, in some embodiments, a water insoluble conjugated polymer is a copolymer of two or more repeating units. For example, a water insoluble conjugated polymer can be constructed of two or more monomeric species selected from the group consisting of D and A monomeric species described herein. In some embodiments, a water insoluble conjugated polymer is a copolymer of a donor-acceptor (D-A) architecture. In some embodiments, for example, a D-A water insoluble conjugated polymer is composed of cyclopentadithiophene and 2,1,3-benzothiadiazole (PCPDTBT) or cyclopentadithiophene and 2,1,3-benzoselenadiazole (PCPDTBSe). In some embodiments, a water insoluble conjugated polymer has the structure of Formula (I):

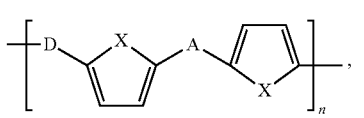

wherein D is a donor monomeric species described herein, A is an acceptor monomeric species described herein, and each X is independently O, N, S or Se.

In some embodiment, a composition described herein comprises one or more D-A conjugated polymers in an aqueous medium. For example, a composition can comprise any combination of D-A conjugated polymers described herein in an aqueous medium.

In some embodiments, water insoluble conjugated polymers of aqueous solutions described herein are sonicated conjugated polymers. Sonication of a water insoluble conjugated polymer, in some embodiments, can induce or result in one or more conformational and/or structural changes of the conjugated polymer, thereby permitting the water insoluble conjugated polymer to become water soluble or substantially water soluble and serve as a solute.

As described herein, water insoluble conjugated polymeric solute of aqueous solutions, in some embodiments, are not modified with one or more chemical species operable to increase the aqueous solubility or dispersibility of the conjugated polymer. For example, water insoluble conjugated polymers of aqueous solutions described herein are not grafted or chemically functionalized with one or more hydrophilic chemical functionalities or species. Moreover, in some embodiments, hydrophilic functional groups and/or structures, in some embodiments, are not provided to the water insoluble conjugated polymers by acid/base reactions and/or reduction-oxidation (redox) reactions.

Further, in some embodiments, the aqueous solvent does not comprise chemical species operable to increase the solubility or dispersibility of the water insoluble conjugated polymers. In some embodiments, for example, the aqueous solvent does not comprise surfactants or other dispersing agents for interaction with or modification of the water insoluble conjugated polymer to increase conjugated polymer aqueous solubility.

In some embodiments, water insoluble conjugated polymers are not modified with one or more chemical species operable to increase the aqueous solubility or dispersibility of the conjugated polymer in an amount between about 0.001 percent and about 1 percent. In some embodiments, water insoluble conjugated polymers are not modified with one or more chemical species operable to increase the aqueous solubility or dispersibility of the conjugated polymer in excess of 1 percent or 2 percent.

Alternatively, in some embodiments described herein, water insoluble conjugated polymer can be modified with one or more chemical species operable to increase the aqueous solubility or dispersibility of the conjugated polymer. In some embodiments, for example, a water insoluble conjugated polymer is at least partially encapsulated by a dispersing agent. Any dispersing agent not inconsistent with the objectives of the present invention may be used. In some embodiments, for instance, a dispersing agent comprises a surfactant, such as an anionic surfactant or cationic surfactant. In some embodiments, a surfactant comprises a zwitterionic surfactant or a nonionic surfactant. A nonionic surfactant, in some embodiments, comprises an alcohol, including a fatty alcohol, a polyol, a polyoxyethylene glycol (PEG) alkyl ether (or a PEG alkylphenol ether), a polyoxypropylene glycol alkyl ether, a glucoside alkyl ether, a glycerol alkyl ester, a sorbitan alkyl ester or a combination thereof. In some embodiments, a dispersing agent comprises a phospholipid or phospholipid derivative such as a PEG phospholipid.

Further, as described herein, a dispersing agent can comprise a labeling agent. Suitable labeling agents can comprise light emitting species, such as a fluorescent or phosphorescent species. A light emitting species of a dispersing agent described herein, in some embodiments, is chemically bonded or conjugated to the dispersing agent, including at the surface of the dispersing agent. For example, in some embodiments, a light emitting species is chemically bonded or conjugated to a phospholipid described herein. Any light emitting species not inconsistent with the objectives of the present invention may be used. In some embodiments, a light emitting species emits electromagnetic radiation having a visible wavelength. In other embodiments, a light emitting species emits electromagnetic radiation having an infrared (IR) wavelength, such as a near infrared (NIR) wavelength, a short IR (SWIR) wavelength, a mid IR (MWIR) wavelength or a long IR (LWIR) wavelength. In some embodiments, a light emitting species emits electromagnetic radiation having a microwave wavelength or terahertz radiation. Non-limiting examples of light emitting species suitable for use in some embodiments described herein include laser dyes such as a rhodamine, a fluorescein, a coumarin, or a derivative thereof and fluorescent proteins such as green fluorescent protein (GFP). In some embodiments, a light emitting species comprises fluorescein isothiocyanate (FITC).

Moreover, a light emitting species can be attached or conjugated to a dispersing agent in any manner not inconsistent with the objective of the present invention, including through one or more types of chemical bonding or intermolecular forces described herein. The use of a dispersing agent comprising a light emitting species, in some embodiments, can permit a water insoluble conjugated polymer described herein to be visualized and/or tracked in a biological environment.

Water insoluble conjugated polymer(s) can be present in aqueous solutions described herein in any amount not inconsistent with the objectives of the present invention. In some embodiments, water insoluble conjugated polymer(s) are present as solute in aqueous solutions described herein in an amount provided in Table I.

TABLE I

Amounts of Water Insoluble Polymers in Aqueous Solution
Amount (μg/ml)

| Amount (μg/ml) |
|---|
| 5-30 |
| 10-50 |
| 10-25 |
| 15-20 |
| 50-150 |
| 150-250 |
| 250-500 |
| 500-1,000 |
| >1,000 |

In some embodiments, solute particles of a water insoluble conjugated polymer can have any geometry not inconsistent with the objectives of the present invention. In some embodiments, for example, a water insoluble conjugated polymer is present in the solution as solute particles having an anisotropic geometry. An anisotropic geometry, in some embodiments, comprises an elongated shape such as a tube shape, rod shape, a wire shape, a fiber shape, a rice shape, an ellipsoidal shape, or a more complex amorphous or polyhedral shape. In some embodiments, anisotropic water insoluble conjugated polymer solute particles have an aspect ratio greater than 1 or greater than 10. Aspect ratio, as used herein, is the length of the particle divided by the width or diameter of the particle. In some embodiments, water insoluble conjugated polymer solute particles have an aspect ratio according to Table II.

TABLE II

Aspect Ratios of Water Insoluble Solute Particles
Aspect Ratio

| Aspect Ratio |
|---|
| >5 |
| >15 |
| >50 |
| >100 |
| 5-100 |
| 5-30 |
| 10-80 |
| 15-70 |

Further, solute particles of a water insoluble conjugated polymer can have any size not inconsistent with the objectives of the present invention. In some embodiments, solute particles can have an average width or diameter between about 1 nm and about 500 nm or between about 10 nm and about 100 nm. In some embodiments, solute particles can have an average width or diameter of up to about 50 nm or up to about 30 nm. In some embodiments, solute particles of a water insoluble conjugated polymer have an average width or diameter between about 10 nm and about 50 nm or between about 20 nm and about 30 nm. Moreover, in some embodiments, solute particles can have an average length between about 1 nm and about 10 μm or between about 100 nm and about 1 μm.

In addition, solute particles of a water insoluble conjugated polymer, in some embodiments, are conjugated or attached to one or more active agents, such as one or more targeting agents. An active agent can be conjugated to a water insoluble conjugated polymer in any manner not inconsistent with the objectives of the present invention. For example, in some embodiments, an active agent is associated with the water insoluble conjugated polymer through one or more hydrogen bonding, electrostatic bonding, ionic bonding, dipole-dipole forces, and van der Waals interactions. In other embodiments, the active agent is associated with the water insoluble conjugated polymer through one or more covalent bonds. Further, in some embodiments, the active agent is attached to or associated with the outer surface of the particle of water insoluble conjugated polymer.

In some embodiments, an active agent comprises a targeting agent. Any targeting agent not inconsistent with the objectives of the present invention may be used. In some embodiments, for instance, a targeting agent comprises an antibody, a chemokine receptor, and/or a targeting ligand such as CXCR12 or CXCR4. In some embodiments, a targeting agent comprises a nucleic acid. A nucleic acid, in some embodiments, comprises DNA. In some embodiments, a nucleic acid comprises RNA, including but not limited to siRNA. Further, a nucleic acid can have any structure or morphology not inconsistent with the objectives of the present invention. In some embodiments, for instance, a nucleic acid has a spherical or helical morphology. In addition, in some embodiments, a targeting agent comprises folic acid.

In some embodiments, an active agent comprises a compound that can facilitate binding of a particle of a water insoluble conjugated polymer to a tumor, biofilm, bacterial matrix, or extracellular matrix. For example, in some embodiments, an active agent comprises a glucan or glycan such as dextran, dextran sulfate, heparin or heparin sulfate; a structural protein such as laminin; an amino acid such as lysine; and/or a growth factor such as vascular endothelial growth factor (VEGF) or fibroblast growth factor (FGF).

Further, in some embodiments, an active agent comprises a compound that can degrade or substantially degrade one or more extracellular matrix components. For example, in some embodiments, an active agent comprises an enzyme. Any enzyme not inconsistent with the objectives of the present invention may be used. In some embodiments, for example, an enzyme comprises collagenase, trypsin or papain.

In some embodiments, an active agent comprises a light emitting species, such as a light emitting species described hereinabove. In some embodiments, a light emitting species comprises a fluorescent or bioluminescent polymer.

Additionally, in some embodiments, an active agent comprises a chemotherapeutic agent. Any chemotherapeutic agent not inconsistent with the objectives of the present invention may be used. A chemotherapeutic agent, for reference purposes herein, can include an agent for treating cancer or an agent for treating a bacterial infection. In some embodiments, for instance, a chemotherapeutic agent comprises an anti-cancer agent. In some embodiments, a chemotherapeutic agent comprises an anti-bacterial agent. Moreover, a chemotherapeutic agent described herein, in some embodiments, can be active at normothermic or hyperthermic temperatures.

In some embodiments, an active agent comprises a metal nanoparticle. Any metal nanoparticle not inconsistent with the objectives of the present invention may be used. In some embodiments, for example, a metal nanoparticle comprises Au, Ag, Cu, Pd, or Pt. In some embodiments comprising a plurality of metal nanoparticles attached to a particle of water insoluble conjugated polymer, the particle of water insoluble conjugated polymer can be larger than the metal nanoparticles and can form a composite material comprising a single polymer particle decorated, surrounded or substantially surrounded with the plurality of metal nanoparticles. In some embodiments, a metal nanoparticle can be attached or conjugated to a water insoluble conjugated polymer described herein before or after the polymer is in particle form. In some embodiments, for instance, one or more metal nanoparticles can be attached to a water insoluble conjugated polymer in straight chain form, followed by sonication to provide polymer particles comprising the metal nanoparticles. Further, as described herein, a metal nanoparticle can be attached or conjugated to a water insoluble conjugated polymer in any manner not inconsistent with the objectives of the present invention. In some embodiments, a metal nanoparticle is associated with the water insoluble conjugated polymer through one or more of hydrogen bonding, electrostatic bonding, ionic bonding, dipole-dipole forces, and van der Waals interactions. In other embodiments, the metal nanoparticle is associated with the water insoluble conjugated polymer through one or more covalent bonds. In some embodiments, for example, a ligand or surface capping agent of the nanoparticle can be covalently incorporated into the water insoluble conjugated polymer, including but not limited to as a pendant group of the water insoluble conjugated polymer. The use of an active agent comprising a metal nanoparticle, in some embodiments, can modulate the electric field adjacent to the particle, thereby enhancing the thermal ablation properties of the particle of water insoluble conjugated polymer.

In some embodiments, water insoluble conjugated polymers of aqueous solutions described herein are not cytotoxic or are not substantially cytotoxic, thereby permitting use in various biological applications. Further, in some embodiments, aqueous solutions described herein can be lyophilized and the water insoluble conjugated polymer re-solubilized in aqueous solvent at a later date.

Additionally, in some embodiments, aqueous solutions described herein comprising water insoluble conjugated polymers are stable at room temperature for a time period of at least 2 weeks or at least 1 month. In some embodiments, the aqueous solutions are stable for at least 6 months or at least 1 year.

Aqueous solutions described herein, in some embodiments, are also stable over a wide temperature range. For example, in some embodiments, aqueous solutions described herein are stable over a temperature range of 3° C. to 60° C. and/or stable to thermal cycling.

Surprisingly, water insoluble conjugated polymer solute of aqueous solutions described herein is stable and/or resistant to degradation over one or more of the foregoing time periods and/or temperature ranges. For example, minimal changes to the absorption spectra of the conjugated polymers over time and temperature fluctuations provide evidence of conjugated polymer stability in the aqueous solution.

In some embodiments, an aqueous solution described herein comprising water insoluble conjugated polymer solute demonstrates an increase in temperature when irradiated with electromagnetic radiation of wavelength matching or substantially matching the absorption maximum of the conjugated polymer, the increase in temperature being at least five times or at least ten times greater than an increase in temperature of water irradiated under conditions matching the conjugated polymer irradiation, wherein the conjugated polymer is present in an amount ranging from about 1 ng/ml to about 100 mg/ml. In some embodiments, the increase in temperature is at least 15 times or 20 times greater than an increase in temperature of water irradiated under matching conditions. Further, in some embodiments, the water insoluble conjugated polymer is present in an amount ranging from about 5 µg/ml to about 120 µg/ml, from about 5 µg/ml to about 30 µg/ml, from about 30 µg/ml to about 50 µg/ml or from about 50 µg/ml to about 100 µg/ml to provide any of the foregoing temperature increases.

II. Colloidal Compositions of Water Insoluble Conjugated Polymers

In another aspect, colloidal compositions are described herein. A colloidal composition, in some embodiments, comprises an aqueous or aqueous-based continuous phase and a dispersed phase comprising at least one water insoluble conjugated polymer, wherein the water insoluble conjugated polymer is not modified with one or more chemical species operable to increase the aqueous solubility or dispersibility of the conjugated polymer.

Alternatively, in other embodiments, a colloidal composition comprises an aqueous or aqueous-based continuous phase and a dispersed phase comprising at least one water insoluble conjugated polymer, wherein the water insoluble conjugated polymer is at least partially encapsulated by a dispersing agent. The dispersing agent, in some embodiments, is non-covalently associated with the water insoluble conjugated polymer. For example, in some embodiments, a dispersing agent is associated with the water insoluble conjugated polymer through one or more of hydrogen bonding, electrostatic bonding, ionic bonding, dipole-dipole forces, and van der Waals interactions. In other embodiments, the dispersing agent is associated with the water insoluble conjugated polymer through one or more covalent bonds. In addition, in some embodiments, a dispersing agent described herein further comprises a light emitting species.

Turning now to specific components, colloidal compositions described herein comprise an aqueous or aqueous-based continuous phase. In some embodiments, the continuous phase is water. In some embodiments, the continuous phase comprises water and one or more chemical species. In some embodiments wherein the aqueous-based continuous phase comprises chemical species in addition to water, the chemical species are not operable to increase the aqueous solubility or dispersibility of the water insoluble conjugated polymer.

Any suitable water insoluble electrically conductive conjugated polymer not inconsistent with the objectives of the present invention can be used as the dispersed phase. In some embodiments, water insoluble conjugated polymers of colloidal compositions are selected from the water insoluble conjugated polymers described in Section I herein in conjunction with FIGS. 1 and 2.

As described herein, water insoluble conjugated polymeric dispersed phase of colloidal compositions, in some embodiments, is not modified with one or more chemical species operable to increase the aqueous solubility or dispersibility of the conjugated polymer. For example, water insoluble conjugated polymers of colloidal compositions described herein are not grafted or chemically functionalized with one or more hydrophilic chemical functionalities or species. Moreover, in some embodiments, hydrophilic functional groups and/or structures, in some embodiments, are not provided to the water insoluble conjugated polymers by acid/base reactions and/or reduction-oxidation (redox) reactions.

Further, in some embodiments, the aqueous or aqueous-based continuous phase does not comprise chemical species operable to increase the solubility or dispersibility of the water insoluble conjugated polymer. In some embodiments, for example, the aqueous continuous phase does not comprise surfactants or other dispersing agents for interaction with or modification of the water insoluble conjugated polymer to increase conjugated polymer aqueous solubility or dispersibility.

In some embodiments, water insoluble conjugated polymers are not modified with one or more chemical species operable to increase the aqueous solubility or dispersibility of the conjugated polymer in an amount between about 0.001 percent and about 1 percent. In some embodiments, water insoluble conjugated polymers are not modified with one or more chemical species operable to increase the aqueous solubility or dispersibility of the conjugated polymer in excess of 1 percent or 2 percent.

Alternatively, as described herein, a water insoluble conjugated polymer of some colloidal compositions can be associated with or modified by a chemical species operable to increase the aqueous solubility or dispersibility of the conjugated polymer. In some embodiments, for example, a water insoluble conjugated polymer is at least partially encapsulated by a dispersing agent. Any dispersing agent not inconsistent with the objectives of the present invention may be used. In some embodiments, for instance, a dispersing agent comprises a surfactant, such as an anionic or cationic surfactant. In some embodiments, a surfactant comprises a zwitterionic surfactant or a nonionic surfactant. A nonionic surfactant, in some embodiments, comprises an alcohol, including a fatty alcohol, a polyol, a polyoxyethylene glycol alkyl ether (or a PEG alkylphenol ether), a polyoxypropylene glycol alkyl ether, a glucoside alkyl ether, a glycerol alkyl ester, a sorbitan alkyl ester or a combination thereof. In some embodiments, a dispersing agent comprises a phospholipid or phospholipid derivative such as a PEG phospholipid.

Further, as described herein, a dispersing agent can comprise a labeling agent. Suitable labeling agents can comprise light emitting species, including fluorescent or phosphorescent species. A light emitting species of a dispersing agent described herein, in some embodiments, is chemically bonded or conjugated to the dispersing agent, including at the surface of the dispersing agent. For example, in some embodiments, a light emitting species is chemically bonded or conjugated to a phospholipid described herein. Any light emitting species not inconsistent with the objectives of the present invention may be used. In some embodiments, a light emitting species emits electromagnetic radiation having a visible wavelength. In other embodiments, a light emitting species emits electromagnetic radiation having an infrared (IR) wavelength, such as a near infrared (NIR) wavelength, a short IR (SWIR) wavelength, a mid IR (MWIR) wavelength or a long IR (LWIR) wavelength. In some embodiments, a light emitting species emits electromagnetic radiation having a microwave wavelength or terahertz radiation. Non-limiting examples of light emitting species suitable for use in some embodiments described herein include laser dyes such as a rhodamine, a fluorescein, a coumarin, or a derivative thereof and fluorescent proteins such as green fluorescent protein (GFP). In some embodiments, a light emitting species comprises fluorescein isothiocyanate (FITC).

Moreover, a light emitting species can be attached or conjugated to a dispersing agent in any manner not inconsistent with the objective of the present invention, including through one or more types of chemical bonding or intermolecular forces described herein. The use of a dispersing agent comprising a light emitting species, in some embodiments, can permit a water insoluble conjugated polymer described herein to be visualized and/or tracked in a biological environment.

Water insoluble conjugated polymer(s) can be present in colloidal compositions described herein in any amount not inconsistent with the objectives of the present invention. In some embodiments, water insoluble conjugated polymer(s) are present as a dispersed phase in an aqueous or aqueous-based continuous phase in an amount provided in Table I hereinabove.

In some embodiments, dispersed particles of a water insoluble conjugated polymer can have any geometry not inconsistent with the objectives of the present invention. In some embodiments, for example, a water insoluble conjugated polymer is present in the composition as dispersed or colloidal particles having an anisotropic geometry. An anisotropic geometry, in some embodiments, comprises an elongated shape such as a rod shape, a wire shape, a fiber shape, a rice shape, an ellipsoidal shape, or a more complex amorphous or polyhedral shape. In some embodiments, anisotropic dispersed particles have an aspect ratio greater than 1 or greater than 10. In some embodiments, water insoluble conjugated polymer particles of the dispersed phase have an aspect ratio according to Table II hereinabove.

Further, dispersed particles of a water insoluble conjugated polymer can have any size not inconsistent with the objectives of the present invention. In some embodiments, dispersed particles can have an average width or diameter between about 1 nm and about 500 nm or between about 10 nm and about 100 nm. In some embodiments, dispersed particles of a water insoluble conjugated polymer have an average particle size less than 200 nm or less than 150 nm. In some embodiments, dispersed particles have an average particle size ranging from about 50 nm to about 200 nm or from about 75 nm to about 150 nm. Dispersed particles of water insoluble conjugated polymer, in some embodiments, have an average size ranging from about 5 nm to about 50 nm. In some embodiments, dispersed particles can have an average width or diameter of up to about 50 nm or up to about 30 nm. In some embodiments, dispersed particles of a water insoluble conjugated polymer have an average width or diameter between about 10 nm and about 50 nm or between about 20 nm and about 30 nm. Moreover, in some embodiments, dispersed particles can have an average length between about 1 nm and about 10 μm or between about 100 nm and about 1 μm.

In addition, dispersed particles of a water insoluble conjugated polymer, in some embodiments, are conjugated or attached to one or more active agents, such as one or more targeting agents. An active agent can be conjugated to a water insoluble conjugated polymer in any manner not inconsistent with the objectives of the present invention. For example, in some embodiments, an active agent is associated with the water insoluble conjugated polymer through one or more of hydrogen bonding, electrostatic bonding, ionic bonding, dipole-dipole forces, and van der Waals interactions. In other embodiments, the active agent is associated with the water insoluble conjugated polymer through one or more covalent bonds. Further, in some embodiments, the active agent is attached to or associated with the outer surface of the particle of water insoluble conjugated polymer.

In some embodiments, an active agent comprises a targeting agent. Any targeting agent not inconsistent with the objectives of the present invention may be used. In some embodiments, for instance, a targeting agent comprises an antibody, a chemokine receptor, and/or a targeting ligand such as CXCR12 or CXCR4. In some embodiments, a targeting agent comprises a nucleic acid. A nucleic acid, in some embodiments, comprises DNA. In some embodiments, a nucleic acid comprises RNA, including but not limited to siRNA. Further, a nucleic acid can have any structure or morphology not inconsistent with the objectives of the present invention. In some embodiments, for instance, a nucleic acid has a spherical or helical morphology. In addition, n some embodiments, a targeting agent comprises folic acid.

In some embodiments, an active agent comprises a compound that can facilitate binding of a particle of a water insoluble conjugated polymer to a tumor, biofilm, bacterial matrix, or extracellular matrix. For example, in some embodiments, an active agent comprises a glucan or glycan such as dextran, dextran sulfate, heparin or heparin sulfate; a structural protein such as laminin; an amino acid such as lysine; and/or a growth factor such as vascular endothelial growth factor (VEGF) or fibroblast growth factor (FGF).

Further, in some embodiments, an active agent comprises a compound that can degrade or substantially degrade one or more extracellular matrix components. For example, in some embodiments, an active agent comprises an enzyme. Any enzyme not inconsistent with the objectives of the present invention may be used. In some embodiments, for example, an enzyme comprises collagenase, trypsin or papain.

In some embodiments, an active agent comprises a light emitting species, such as a light emitting species described hereinabove. In some embodiments, a light emitting species comprises a fluorescent or bioluminescent polymer.

Additionally, in some embodiments, an active agent comprises a chemotherapeutic agent. Any chemotherapeutic agent not inconsistent with the objectives of the present invention may be used. For example, a chemotherapeutic agent can include an agent for treating cancer and/or an agent for treating a bacterial infection. In some embodiments, a chemotherapeutic agent comprises an anti-cancer agent. In some embodiments, a chemotherapeutic agent comprises an anti-bacterial agent. Moreover, a chemotherapeutic agent described herein, in some embodiments, can be active at normothermic or hyperthermic temperatures.

In some embodiments, an active agent comprises a metal nanoparticle. Any metal nanoparticle not inconsistent with the objectives of the present invention may be used. In some embodiments, for example, a metal nanoparticle comprises Au, Ag, Cu, Pd, or Pt. In some embodiments comprising a plurality of metal nanoparticles attached to a particle of water insoluble conjugated polymer, the particle of water insoluble conjugated polymer can be larger than the metal nanoparticles and can form a composite material comprising a single polymer particle decorated, surrounded or substantially surrounded with the plurality of metal nanoparticles. In some embodiments, a metal nanoparticle can be attached or conjugated to a water insoluble conjugated polymer described herein before or after the polymer is in particle form. In some embodiments, for instance, one or more metal nanoparticles can be attached to a water insoluble conjugated polymer in straight chain form, followed by sonication to provide polymer particles comprising the metal nanoparticles. Further, as described herein, a metal nanoparticle can be attached or conjugated to a water insoluble conjugated polymer in any manner not inconsistent with the objectives of the present invention. In some embodiments, a metal nanoparticle is associated with the water insoluble conjugated polymer through one or more of hydrogen bonding, electrostatic bonding, ionic bonding, dipole-dipole forces, and van der Waals interactions. In other embodiments, the metal nanoparticle is associated with the water insoluble conjugated polymer through one or more covalent bonds. In some embodiments, for example, a ligand or surface capping agent of the nanoparticle can be covalently incorporated into the water insoluble conjugated polymer, including but not limited to as a pendant group of the water insoluble conjugated polymer. The use of an active agent comprising a metal nanoparticle, in some embodiments, can modulate the electric field adjacent to the particle, thereby enhancing the thermal ablation properties of the particle of water insoluble conjugated polymer.

In some embodiments, water insoluble conjugated polymers of colloidal compositions described herein are not cytotoxic or are not substantially cytotoxic, thereby permitting use in various biological applications. Further, in some embodiments, colloidal compositions described herein can be lyophilized and the water insoluble conjugated polymer re-dispersed in aqueous continuous phase at a later date.

Additionally, in some embodiments, colloidal compositions described herein comprising water insoluble conjugated polymers are stable at room temperature for a time period of at least 2 weeks or at least 1 month. In some embodiments, the colloidal compositions are stable for at least 6 months or at least 1 year.

Colloidal compositions described herein, in some embodiments, are also stable over a wide temperature range. For example, in some embodiments, colloidal compositions described herein are stable over a temperature range of 3° C. to 60° C. and/or stable to thermal cycling.

Surprisingly, dispersed water insoluble conjugated polymer of colloidal compositions described herein is stable and/or resistant to degradation over one or more of the foregoing time periods and/or temperature ranges. For example, minimal changes to the absorption spectra of the conjugated polymers over time and temperature fluctuations provide evidence of conjugated polymer stability in the aqueous colloidal composition.

In some embodiments, a colloidal composition described herein comprising a water insoluble conjugated polymer dispersed phase demonstrates an increase in temperature when irradiated with electromagnetic radiation of wavelength matching or substantially matching the absorption maximum of the conjugated polymer, the increase in temperature being at least five times or at least ten times greater than an increase in temperature of water irradiated under conditions matching the conjugated polymer irradiation wherein the conjugated polymer is present in an amount ranging from about 1 ng/ml to about 100 mg/ml. In some embodiments, the increase in temperature is at least 15 times or 20 times greater than an increase in temperature of water irradiated under matching conditions. Further, in some embodiments, the water insoluble conjugated polymer is present in an amount ranging from about 5 µg/ml to about 120 µg/ml, from about 5 µg/ml to about 30 µg/ml, from about 30 µg/ml to about 50 µg/ml or from about 50 µg/ml to about 100 µg/ml to provide any of the foregoing temperature changes.

In some embodiments, colloidal compositions demonstrating any of the foregoing temperature changes upon irradiation, can further comprise one or more chemical species operable to increase the solubility or dispersibility of the water insoluble conjugated polymer, as described hereinabove. In some embodiments, for example, the water insoluble conjugated polymer is grafted or chemically functionalized with one or more hydrophilic chemical species or functional groups. In some embodiments, hydrophilic functionalization is provided by acid/base reaction(s) or pH changes/variations. Hydrophilic functionalization, in some embodiments, is induced by redox reaction(s) or exposure of the conjugated polymer to ionizing radiation. Further, is some embodiments, the continuous aqueous phase comprises one or more chemical species operable to interact with the conjugated polymer to increase aqueous solubility or dispersibility of the conjugated polymer. In some embodiments, for example, the aqueous continuous phase comprises surfactant or dispersing agents. The aqueous continuous phase, in some embodiments, comprises a chemical species operable to participate in an acid/base or redox reaction(s) with the water insoluble conjugated polymer to increase the aqueous solubility of dispersibility of the conjugated polymer. Additionally, as described herein, colloidal compositions demonstrating any of the foregoing temperature changes upon irradiation, in some embodiments, do not comprise one or more chemical species operable to increase the solubility or dispersibility of the water insoluble conjugated polymer.

III. Methods of Making Aqueous Solutions and Colloidal Compositions

In another aspect, methods of making aqueous solutions of water insoluble conjugated polymers are described herein. In some embodiments, a method of making an aqueous solution comprises providing an organic solution phase comprising a water insoluble conjugated polymer in an organic solvent, providing an aqueous phase in contact with the organic solution phase and solubilizing at least some of the water insoluble conjugated polymer in the aqueous phase by sonication and evaporation of the organic solvent to provide the aqueous solution, wherein the water insoluble conjugated polymer is not modified with one or more chemical species operable to increase the aqueous solubility or dispersibility of the conjugated polymer. Sonication of a water insoluble polymer, in some embodiments, can induce or result in one or more conformational and/or structural changes of the conjugated polymer, thereby permitting the water insoluble conjugated polymer to become water soluble, substantially water soluble or partially water soluble.

A method of making an aqueous solution, in other embodiments, comprises providing an organic phase comprising a solution of a water insoluble conjugated polymer in an organic solvent, providing an aqueous phase in contact with the organic phase and solubilizing at least some of the water insoluble conjugated polymer in the aqueous phase by sonicating and/or evaporating the organic solvent to provide the aqueous solution, wherein the aqueous phase comprises at least one dispersing agent and the water insoluble conjugated polymer is at least partially encapsulated by the dispersing agent.

In some embodiments, the aqueous solution provided by a method described herein is filtered subsequent to sonication and/or evaporation of the organic solvent to remove any water insoluble conjugated polymer not solubilized in the aqueous phase. In some embodiments, the aqueous solution is centrifuged subsequent to sonication and/or evaporation to separate or remove particles of water insoluble conjugated polymer having a size or shape within a desired size or shape range. For example, in some embodiments, a method further comprises centrifuging an aqueous solution to separate first solute particles of the water insoluble conjugated polymer having a first size and first aspect ratio from second solute particles of the water insoluble conjugated polymer having a second size and second aspect ratio.

Further, aqueous solutions made according to methods described herein can have any of the compositional, chemical and/or physical properties provided in Section I hereinabove for aqueous solutions of water insoluble conjugated polymers.

In another aspect, methods of making colloidal compositions are described herein. A method of making a colloidal composition, in some embodiments, comprises providing an organic solution phase comprising a water insoluble conjugated polymer in an organic solvent, providing an aqueous phase in contact with the organic solution phase and dispersing at least some of the water insoluble polymer in the aqueous phase by sonication and evaporation of the organic solvent to provide the colloidal composition, wherein the water insoluble conjugated polymer is not modified with one or more chemical species operable to increase the aqueous or solubility or dispersibility of the conjugated polymer. Sonication of a water insoluble polymer, in some embodiments, can induce or result in one or more conformational and/or structural changes of the conjugated polymer, thereby permitting dispersion of particles of the water insoluble conjugated polymer in an aqueous continuous phase for colloid formation.

A method of making a colloidal composition, in other embodiments, comprises providing an organic phase comprising a solution of a water insoluble conjugated polymer in an organic solvent, providing an aqueous phase in contact with the organic phase and dispersing at least some of the water insoluble conjugated polymer in the aqueous phase by sonication and/or evaporation of the organic solvent to provide the colloidal composition, wherein the aqueous phase comprises at least one dispersing agent and the water insoluble conjugated polymer is at least partially encapsulated by the dispersing agent.

In some embodiments, a colloidal composition described herein is filtered subsequent to sonication and evaporation of the organic solvent to remove any water insoluble conjugated polymer not dispersed in the aqueous phase. In some embodiments, the colloidal composition is centrifuged subsequent to sonication and/or evaporation to separate or remove particles of water insoluble conjugated polymer having a size or shape within a desired size or shape range. For example, in some embodiments, a method further comprises centrifuging a colloidal composition to separate first dispersed particles of the water insoluble conjugated polymer having a first size and first aspect ratio from second dispersed particles of the water insoluble conjugated polymer having a second size and second aspect ratio.

Further, colloid compositions made according to methods described herein can have any of the compositional, chemical and/or physical properties provided in Section II hereinabove for colloidal compositions.

IV. Methods of Treating Diseased Tissue

In another aspect, methods of treating diseased tissue with aqueous media comprising conjugated polymers are described herein. In some embodiments, a method of treating diseased tissue comprises providing an aqueous solution described herein comprising a water insoluble conjugated polymer and disposing the aqueous solution in the diseased tissue. Thermal energy is provided to the diseased tissue by irradiating the conjugated polymer. In some embodiments, thermal energy is provided to the diseased tissue by exposing the conjugated polymer to ultrasound. In some embodiments, hyperthermia and/or other cellular death mechanisms are induced in the diseased tissue from the induced heating resulting in ablation or killing of cells of the diseased tissue. In some embodiments, aqueous solutions for use in methods of treating diseased tissue described herein can have any of the compositional, chemical and/or physical properties provided in Section I hereinabove for aqueous solutions of water insoluble conjugated polymers.

In some embodiments, a method of treating diseased tissue comprises providing a colloidal composition described herein and disposing the colloidal composition in the diseased tissue. Thermal energy is provided to the diseased tissue by irradiating the conjugated polymer. In some embodiments, thermal energy is provided to the diseased tissue by exposing the conjugated polymer to ultrasound. In some embodiments, hyperthermia and/or other cellular death mechanisms are induced in the diseased tissue from the induced heating resulting in ablation or killing of cells of the diseased tissue. In some embodiments, colloidal compositions for use in methods of treating diseased tissue described herein can have any of the compositional, chemical and/or physical properties provided in Section II hereinabove for colloidal compositions of water insoluble conjugated polymers.

For example, in some embodiments, a method of treating diseased tissue comprises providing a composition described herein and disposing the composition in the diseased tissue, wherein the composition includes an aqueous medium and particles of at least one water insoluble conjugated copolymer in the aqueous medium, the water insoluble conjugated copolymer having a donor-acceptor architecture comprising a donor monomeric species (D) and an acceptor monomeric species (A).

Water insoluble conjugated polymers of aqueous solutions and colloidal compositions described herein can demonstrate low band gaps, thereby permitting absorption of radiation in the near infrared region of the electromagnetic spectrum for thermal energy generation. In some embodiments, for example, conjugated polymers of aqueous solutions and colloidal compositions are exposed to radiation having a wavelength ranging from about 700 nm to about 1100 nm for thermal generation in the ablation or killing of diseased cells. In other embodiments, conjugated polymers of aqueous solutions and colloidal compositions are exposed to radiation having a wavelength ranging from about 300 nm to about 10,000 nm for thermal generation in the ablation or killing of diseased cells.

Moreover, in some embodiments, particles of conjugated polymers described herein can be targeted to specific biological compartments, including through the use of one or more active agents. For example, in some embodiments, polymer particles of a composition described herein are targeted to the extracellular matrix surrounding eukaryotic cells, including diseased cells, or to an extracellular matrix component such as a biofilm.

Methods described herein can be used to treat any diseased tissue not inconsistent with the objectives of the present invention. In some embodiments, diseased tissue comprises tissue that can be clinically treated by hyperthermia. In some embodiments, diseased tissue comprises one or more of soft tissue, hard tissue, diabetic or hypoglycemic tissue, burn tissue, and tumor tissue.

In some embodiments, diseased tissue comprises cancerous tissue. In some embodiments, methods described herein are operable to kill or ablate cancer cells such as colorectal cancer cells. Diseased tissue, in some embodiments, comprises tissue infected with one or more bacteria or microbes. In some embodiments, methods described herein are operable to kill or ablate bacteria cells such a *Staphylococcus aureus* and *Escherichia coli*. In some embodiments, aqueous solutions and/or colloid compositions are disposed in diseased tissue locally and percutaneously.

In addition, in some embodiments, compositions described herein can be used to induce mild hyperthermia (i.e., hyperthermia including a tissue temperature of less than 45° C.). Mild hyperthermia, in some embodiments, can facilitate drug delivery to eukaryotic or prokaryotic cells for the treatment of disease or infection. In some embodiments, mild hyperthermia can promote wound healing, including but not limited to burn healing. For example, in some embodiments, mild hyperthermia provided by a composition described herein can upregulate a wound-healing species, such as fibronectin and/or collagen.

V. Disease Treatment Systems

In another aspect, disease treatment systems are described herein. In some embodiments, a disease treatment system comprises a source of radiation or ultrasound and a composition including an aqueous medium and particles of at least one water insoluble conjugated polymer dispersed in the aqueous medium. The radiation or ultrasound provided by the source of radiation or ultrasound, in some embodiments, at least partially falls within the absorption profile of the water insoluble conjugated polymer. Thus, in some embodiments, a disease treatment system described herein can be used to carry out any method of treating diseased tissue described hereinabove in Section IV.

Turning now to components of disease treatment systems, disease treatment systems described herein comprise a composition including an aqueous medium and particles of at least one water insoluble conjugated polymer in the aqueous medium. Compositions for use in disease treatment systems described herein can have any of the compositional, chemical and/or physical properties provided in Section I hereinabove for aqueous solutions of water insoluble conjugated polymers or in Section II hereinabove for colloidal compositions of water insoluble conjugated polymers. For example, in some embodiments, the water insoluble conjugated polymer of the composition is a copolymer having a donor-acceptor architecture comprising a donor monomeric species (D) and an acceptor monomeric species (A).

Disease treatment systems described herein also comprise a source of radiation or ultrasound. Any source of radiation or ultrasound not inconsistent with the objectives of the present invention may be used. In some embodiments, a source of radiation or ultrasound comprises a source of electromagnetic radiation having an infrared (IR) wavelength, such as a near infrared (NIR) wavelength, a short IR (SWIR) wavelength, a mid IR (MWIR) wavelength or a long IR wavelength (LWIR). In some embodiments, a source of radiation comprises a laser. In some embodiments, a source of radiation comprises a light emitting diode (LED), including a non-laser diode. In some embodiments, a source of ultrasound comprises an ultrasound transducer. In some embodiments, a source of ultrasound comprises a Doppler probe, including a continuous wave (CW) or pulsed wave (PW) probe.

Some embodiments described herein are further illustrated in the following non-limiting examples.

EXAMPLE 1

NIR-Mediated Thermal Ablation of Cancer Cells Using Aqueous Solutions or Colloidal Compositions of Water Insoluble Conjugated Polymers Materials and Methods All reagents were purchased from common commercial sources and used without further purification unless otherwise noted. 4H-Cyclopenta-[1,2-b:5,4-b']dithiophene was purchased from Astar Pharma. THF was dried over Na/benzophenone ketal. 4,4-Bis(2-ethylhexyl)-2,6-bis(trimethylstannyl)-4H-cyclopenta-[2,1-b;3,4-b']dithiophene, 4,7-dibromo-2,1,3-benzothiadiazole and 4,7-dibromo-2,1,3-benzoselenadiazole were synthesized according to their literature procedures (see J. Hou, T. L. Chen, S. Zhang, H.-Y. Chen, Y. Yang, *J. Phys. Chem. C* 2009, 113, 1601-1607; Z. Zhu, D. Waller, R. Gaudiana, M. Morana, D. Muhlbacher, M. Scharber, C. Brabec, *Macromolecules* 2007, 40, 1981-1986; C. W, Bird, G. W. H. Cheeseman, A. A. Sarsfield, *J. Chem. Soc.* 1963, 4767-4770; I. H. Jung, H. Kim, M.-J, Park, B. Kim, J.-H. Park, E. Jeong, H. Y. Woo, S. Yoo, H.-K. Shim, *J. Polym. Sci. Part A: Polym. Chem.* 2010, 48, 1423-1432; X. Li, W. Zeng, Y. Zhang, Q. Hou, W. Yang, Y. Cao, *Eur. Polym. J.* 2005, 41, 2923-2933; and Y. Tsubata, T. Suzuki, T. Miyashi, Y. Yamashita, *J. Org. Chem.* 1992, 57, 6749-6755, the entireties of which are hereby incorporated by reference). Poly[4,4-bis(2-ethylhexyl)-cyclopenta[2,1-b; 3,4-b']dithiophene-2,6-diylalt-2,1,3-benzothiadiazole-4,7-diyl] (PCPDTBT) and poly[4,4-bis(2-ethylhexyl)-cyclopenta[2,1-b;3,4-b']dithiophene-2,6-diylalt-2,1,3-benzoselenadiazole-4,7-diyl] (PCPDTBSe) were synthesized using a Stille coupling procedure under microwave radiation. The polymerization procedure is outlined below.

Flash chromatography was performed on a Biotage Isolera™ Flash Purification System using Biotage SNAP Flash Purification Cartridges as the stationary phase. Microwave assisted polymerizations were carried out using a CEM Discover Microwave reactor. 300 and 500 MHz $^1$H-NMR spectra were recorded on Bruker Avance DPX-300 and DRX-500 Instruments, respectively. $^{13}$C NMR spectra were recorded on a Bruker Avance DRX-500 instrument at 125.76 MHz, UV-Vis absorption spectra were recorded on an Agilent 8453 diode-array spectrophotometer operating over a range of 190-1100 nm. GC-MS were recorded on an Agilent 6850 Series GC system coupled to an Agilent 5973 mass selective detector run in electron impact mode. Infrared spectra were recorded either on a Mattson Genesis II FT-IR spectrometer or on a Perking Elmer Spectrum 10 spectrometer with an ATR sampling accessory equipped with a diamond anvil. Raman spectra were recorded on a DeltaNu Advantage 532 Raman spectrometer at 532 nm.

Synthesis of PCPDTBT.

4,4-Bis(2-ethylhexyl)-2,6-bis(trimethylstannyl)-4H-cyclopenta-[2,1-b;3,4-b']dithiophene was added to a microwave tube along with 4,7-dibromo-2,1,3-benzothiadiazole (1.05:1 equivalent) and 2 mL of chlorobenzene. The tube was stirred for 5 minutes to dissolve the monomers. Pd(PPh$_3$)$_4$ (2.5 mol %) was then added and the tube was sealed with a crimp cap and placed in a microwave reactor where it was heated to 200° C. for 10 minutes. Upon cooling to room temperature a viscous solution of green polymer was observed in the reaction vessel. The polymer was precipitated in methanol and collected by vacuum filtration. The solid was then transferred to a Soxhlet thimble and subjected to extraction with MeOH (3 hrs), hexanes (6 hrs), and finally chloroform (6 hrs). The chloroform extract was evaporated almost to completion and methanol was added to precipitate the polymer, which was filtered and dried under vacuum for 24 hours. $^1$H-NMR is comparable to the literature values.

Synthesis of PCPDTBSe.

Figure 3:
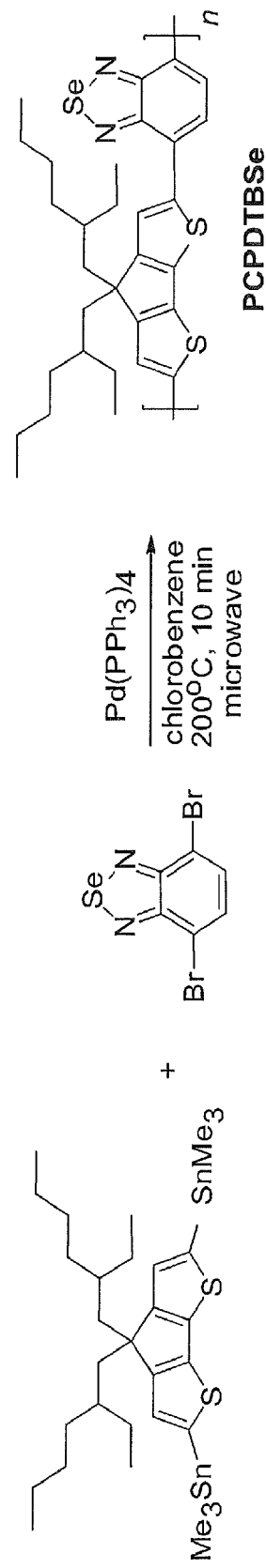
FIG. 3 illustrates a synthetic scheme of a low band gap water insoluble conjugated polymer according to one embodiment described herein.

The synthesis of PCPDTBSe follows the same procedure as PCPDTBT above, except 4,7-dibromo-2,1,3-benzoselenadiazole (1.05:1 equivalent) was used instead of 4,7-dibromo-2,1,3-benzothiadiazole. $^1$H-NMR was comparable to the literature values. The synthetic scheme for PCPDTBSe is provided in FIG. 3.

Formation of Aqueous Solutions or Colloidal Compositions of P3HT, PCPDTBT and PCPDTBSe.

Figure 4:
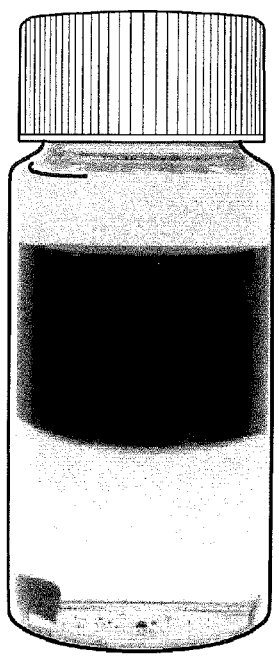
FIG. 4 illustrates aqueous solubilization of a water insoluble conjugated polymer according to one embodiment described herein.
Figure 4:
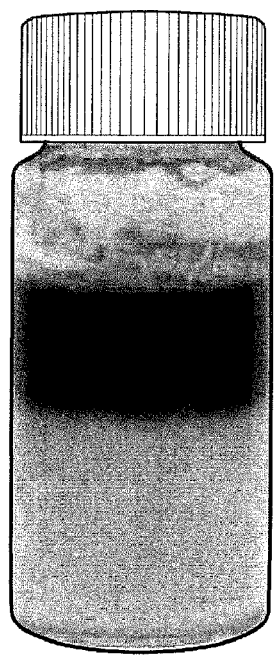
Figure 4:
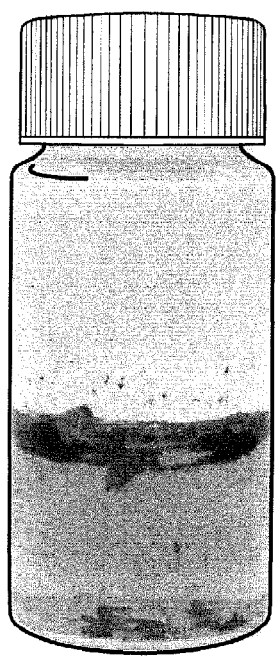
Figure 4:
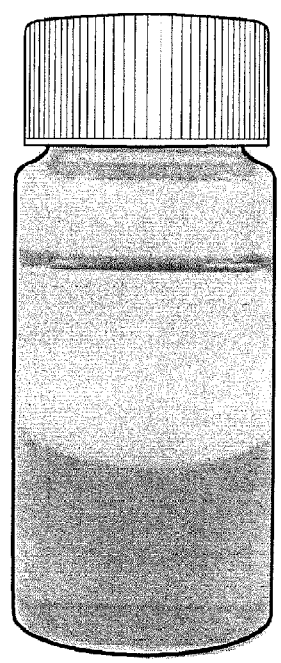

A solution of each polymer in toluene (10 mg/mL) was layered on top of an equal volume of DI water. The layered mixture was water-bath sonicated from 4-24 hrs, until all of the toluene had evaporated. The water layer was filtered to provide an aqueous solution or colloidal composition for each of the water insoluble conjugated polymers. FIG. 4 illustrates solubilization of PCPDTBSe according to the foregoing protocol. FIG. 4(*a*) displays PCPDTBSe dissolved in toluene (top layer) and DI water (bottom layer) while FIG. 4(*b*) demonstrates the results after 1 hour of sonication. FIG. 4(*c*) illustrates completion of sonication and evaporation of the toluene (bottom layer is PCPDTBSe dissolved in water). FIG. 4(*d*) is the aqueous solution of FIG. 4(*c*) after filtration and addition of fresh toluene (top layer). The PCPDTBSe is solubilized in water (bottom layer).

Dynamic Light Scattering of Aqueous Solutions or Colloidal Compositions of P3HT, PCPDTBT and PCPDTBSe.

Aqueous solutions or colloid compositions of P3HT, PCPDTBT and PCPDTBSe nanoparticles were examined. All concentrations were between 0.2 and 0.4 mg/mL in water. P3HT showed a z-average (3 experiments) mean particle diameter size of 146.4 nm with diameters ranging from 32.49-745.4 nm and a polydispersity index (PDI) of 0.209. For PCPDTBT, the z-average particle diameter size was 178.6 nm with diameters ranging from 36.49-663.8 nm and a PDI of 0.207. For PCPDTBSe the z-average particle diameter size was 136.8 nm with diameters ranging from 18.91-593.0 nm and a PDI of 0.222. The results are summarized in Table III.

TABLE III

Dynamic Light Scattering Results

| Polymer | z-average diameter (nm) | Particle diameter range (nm) | PDI |
|---|---|---|---|
| P3HT | 146.4 | 32.49-745.4 | 0.209 |
| PCPDTBT | 178.6 | 36.49-663.8 | 0.207 |
| PCPDTBSe | 136.8 | 18.91-593.0 | 0.222 |

Quantification of P3HT, PCPDTBT and PCPDTBSe Using Absorbance Spectroscopy.

Figure 5:
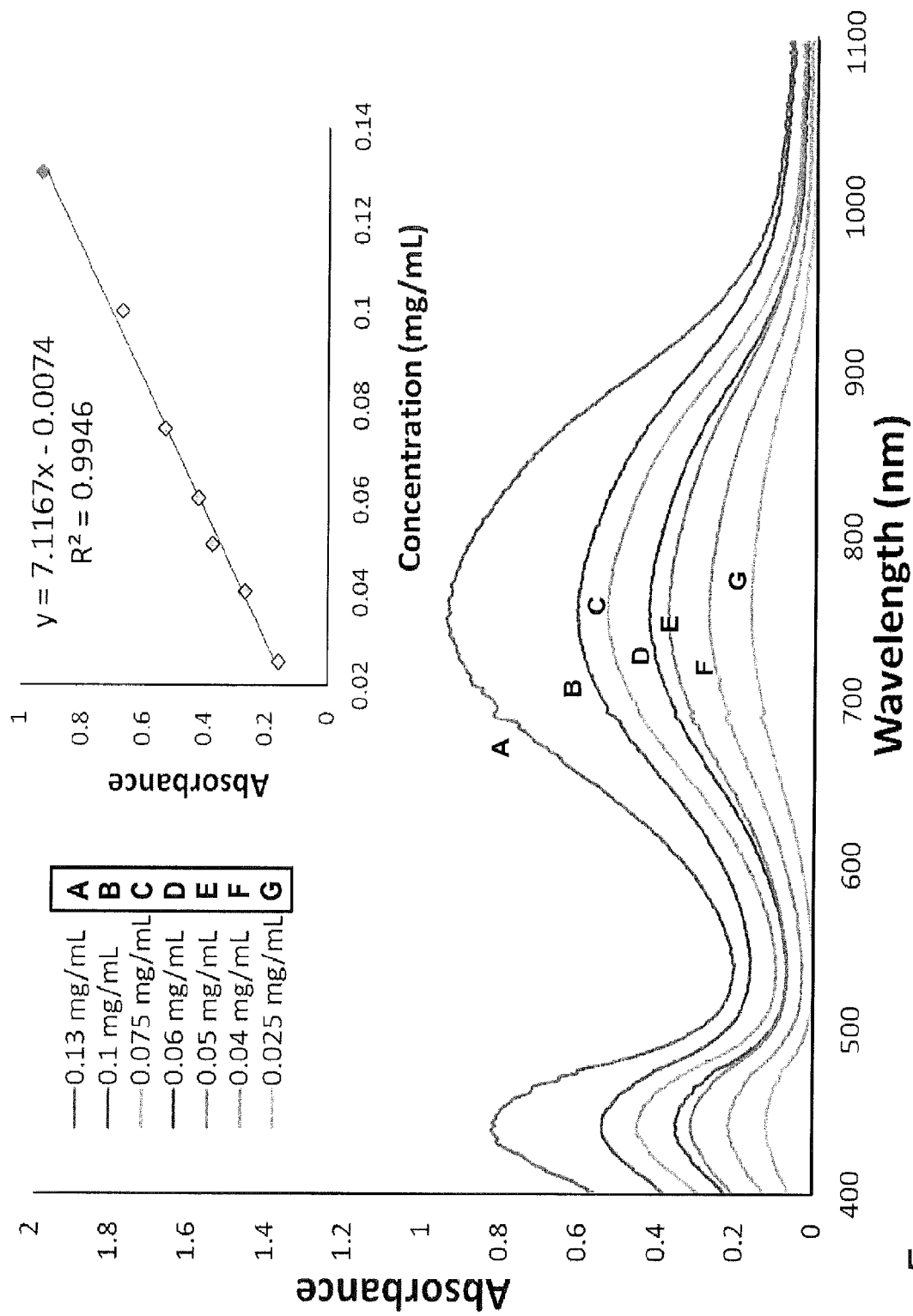
FIG. 5 illustrates aqueous solution concentrations and corresponding absorbance values for a solubilized water insoluble conjugated polymer according to one embodiment described herein.

The concentration of the solubilized water insoluble conjugated polymers in water was determined by centrifugation and lyophilization of half of the above solution to dryness. Once the amount was known the remaining solution was serial diluted and absorbance curves were run at different concentrations. The $\lambda_{max}$ for each concentration was recorded and plotted vs. the concentration. FIG. 5 illustrates aqueous solution concentrations and corresponding absorbance values for PCPDTBSe. Curve A in FIG. 5 is the top curve, and Curve G is the bottom curve, as indicated by the legend in FIG. 5.

Cells and Reagents.

HCT116 and RKO colorectal cancer cell lines were purchased from American Type Culture Collection (ATCC) and cultured in McCoy's medium, supplemented with 2.5 µg/mL amphotericin, 1% L-glutamine, 1% penicillin/streptomycin and 10% fetal bovine serum. Cells were plated into either 6 or 96-well tissue culture dishes at a seeding density of 200,000 or 10,000 cells per well, respectively. Cell viability was measured using a MTS assay (Promega's CellTiter 96 AQueous assay kit). The CellTiter 96AQ is a colorimetric assay that uses [3-(4,5-dimethylthiazol-2-yl)-5-(3-carboxymethoxyphenyl)-2-(4-sulfophenyl)-2H-tetrazolium inner salt, MTS] along with phenazine methosulfate as an electron coupling reagent. Cells will reduce MTS into formazan and the absorbance can be read at 490 nm to provide insight into the activity and viability of live cells.

Heating Methods for Cell Viability.

Adherent cells were used to eliminate any cell settling or turbidity that may impact infrared absorption. Two hundred microliters of either P3HT, PCPDTBT or PCPDTBSe nanoparticles/media solution (0.1 mg/mL) were added for temperature testing and heating of the cells. Cells were placed on a hot water bottle to maintain a temperature of 37° C. during laser application. A Nd:YAG laser (808 nm) operating at 0.6 W of power was used to apply infrared stimulation to the polymer solution for 5 min per sample. A thermocouple measured the temperature of polymer/medium solutions immediately after laser application.

Cell Viability Assays.

Cells were seeded overnight in four ninety-six well plates and grown to ~50% confluency in McCoys 5A medium. The medium was removed and 200 uL of 250 μg/mL, 125 μg/mL, 62 μg/mL, 31 μg/mL stock solutions of P3HT, PCPDTBT or PCPDTBSe in nanoparticle form in medium were added and the plates were incubated at 37° C. for 2 hours prior to laser treatment. Following incubation, infrared treatment was applied for 5 min per well. The medium was replaced with fresh medium and the four plates were incubated at 37° C. for forty-eight hours. Following incubation, cell viability was quantified over a 1.5 hr period using a MTS assay.

Cytotoxicity Assays.

Known concentrations of P3HT, PCPDTBT and PCPDTBSe in nanoparticle form in water were centrifuged and re-suspended in ethanol. The ethanolic solutions were added to 6 well plates (1-5 mL) and allowed to evaporate giving a film of dispersed PCPDTBSe attached to the bottom of the well (250 μg/mL, 125 μg/mL, 62 μg/mL, 31 μg/mL). Cells were then seeded overnight on top of PCPDTBSe at 200,000 cells/well (3 mL). The cells were grown to ~50% confluency in McCoys 5A medium at 37° C. for 24 hrs. An MTS assay was performed by adding a 1:3 mixture of MTS:medium (1 mL) to each well and incubated for 1.5 hrs. A small portion was removed (1 mL) and read in a twenty-four well plate on the plate reader so that the adhered polymer in the six well plate would not interfere with the absorbance readings.

NIR Heating of PCPDTBSe

Figure 6:
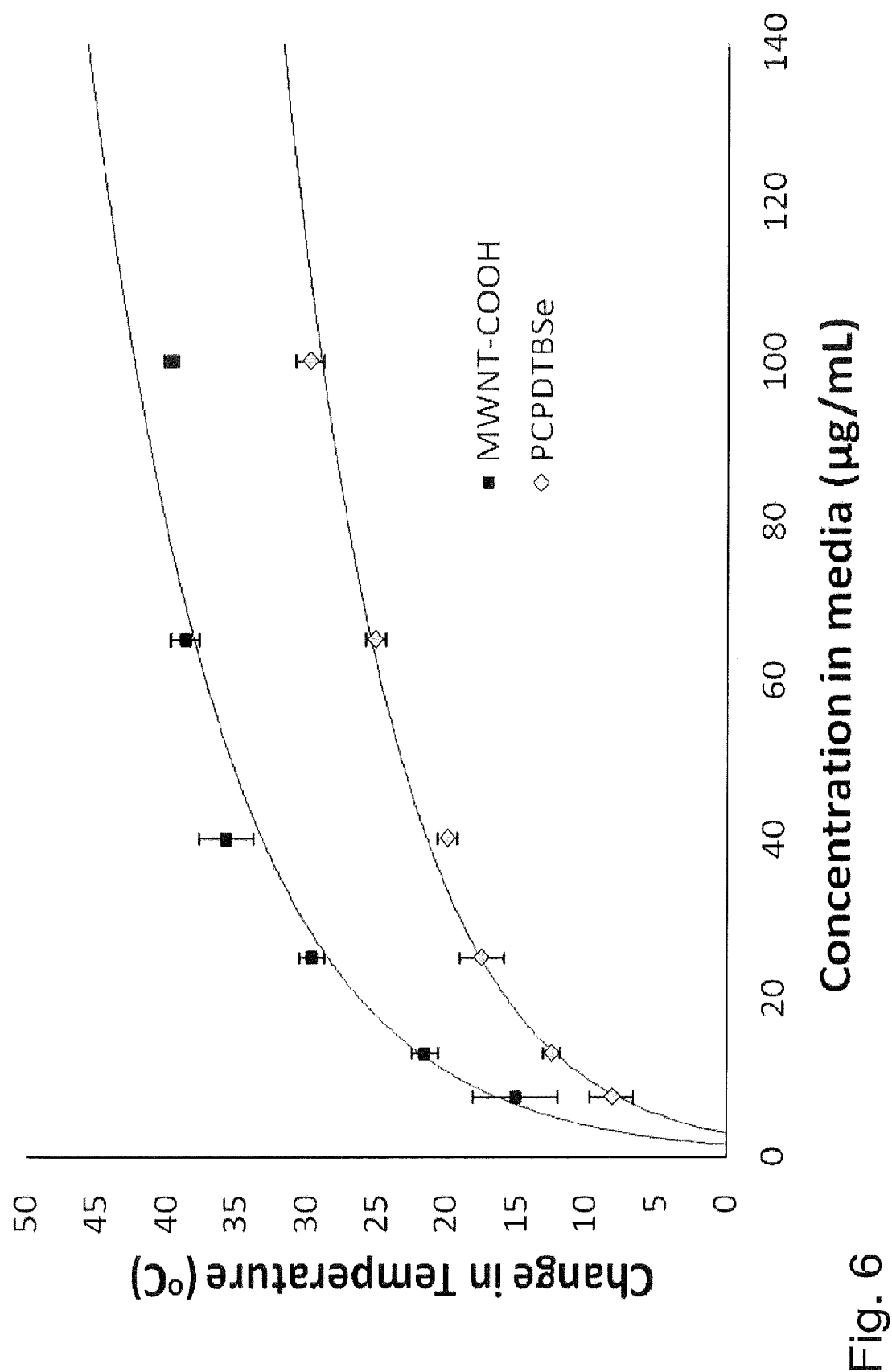
FIG. 6 provides a plot of the change in temperature versus concentration for MWNT-COOH and PCPDTBSe.

In order to test the heating efficacy of PCPDTBSe in nanoparticle form, the PCPDTBSe was compared it to a material that is known to heat well under NIR stimulation. Separate concentrations of oxidized multi-walled carbon nanotubes (MWNT-COOH) were tested along with PCPDTBSe nanoparticles (both in McCoys 5A cell medium) and illuminated with an 808 nm laser (0.6 W) for five minutes. After laser treatment, a thermocouple was used to measure the solution temperature. A plot of the change in temperature vs. concentration for MWNT-COOH and PCPDTBSe nanoparticles is shown in FIG. 6. MWNT-COOH heated faster and to a higher temperature than PCPDTBSe nanoparticles. MWNT-COOH contains metallic portions and has more electrons available for absorption per gram than semiconducting PCPDTBSe nanoparticles, which enhances the heating efficiency of the MWNT-COOH. It required only ~15 μg of MWNT-COOH to change the temperature of the solution by 20° C. after 5 minutes, while it takes PCPDTBSe nanoparticles ~50 μg to achieve the same change.

Cytotoxicity Studies

Figure 7:
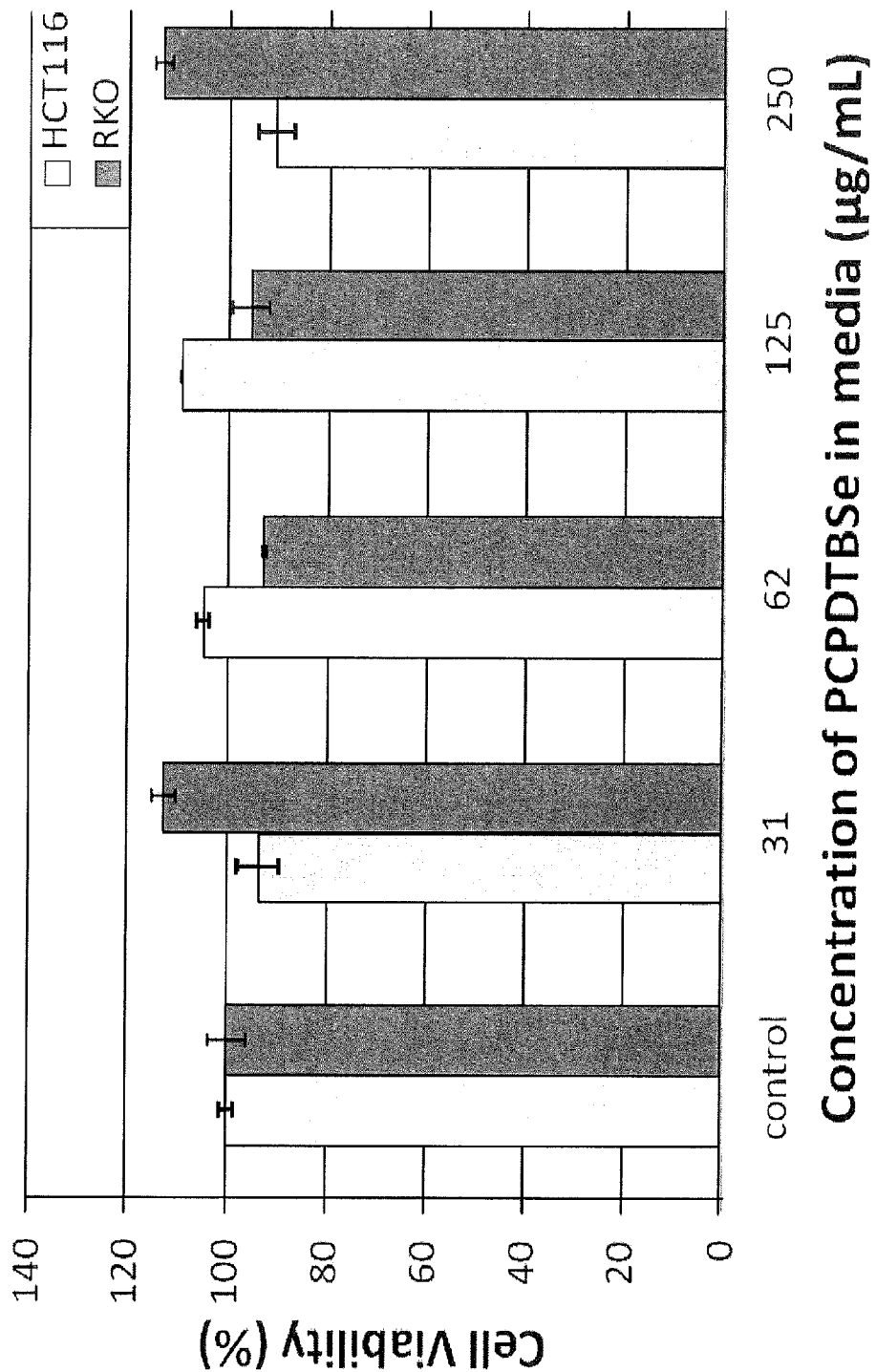
FIG. 7 illustrates results of a cytotoxicity screen of a water insoluble conjugated polymer according to one embodiment described herein.

In order to determine whether PCPDTBSe nanoparticles were harmful to cells, in-vitro cytotoxicity assays were performed in the absence of NIR light. PCPDTBSe nanoparticles in ethanol were coated as a thin film on the bottom of a six well plate at varying concentrations. After evaporation of the solvent, HCT116 and RKO cells were plated at 200,000 cells/well on top of the PCPDTBSe nanoparticle film. The well plates were incubated at 37° C. for 24 hrs. Following incubation, an MTS assay was performed to determine the cell viability compared to a control well normalized to 100% viability. The results of the cytotoxicty screen are provided in FIG. 7. PCPDTBSe nanoparticles showed no significant toxicity towards either HCT116 or RKO cells from 30-250 μg/mL.

Cell Viability Studies

Figure 8:
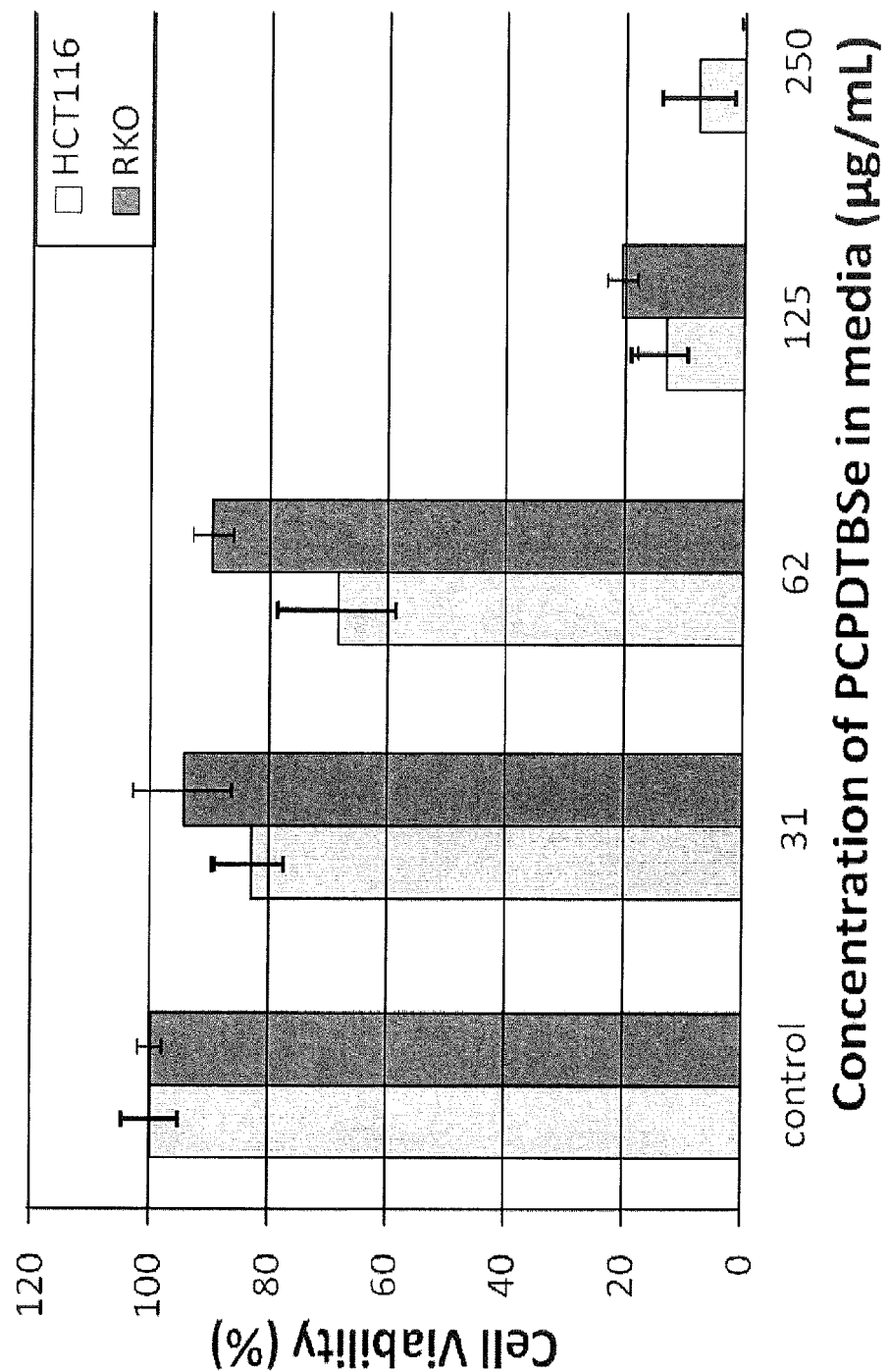
FIG. 8 illustrates results of thermally treating colorectal cancer cells by irradiation of an aqueous solution of a solubilized water insoluble conjugated polymer according to one embodiment described herein.

RKO and HCT colorectal cancer cell lines were used in this study. When NIR radiation is applied to different concentrations of PCPDTBSe nanoparticles in aqueous media, the polymer generates heat which destroys the surrounding cancer cells. An 808 nm laser generating 0.6 W of power was irradiated onto aqueous solutions of PCPDTBSe nanoparticles in media containing RKO and HCT116 cells for 5 minutes at four different concentrations. The results are shown in FIG. 8. The control was well normalized to 100% viability, and error bars are shown as standard deviation of the mean (3 wells). For 31 μg/mL of PCPDTBSe nanoparticles in media, cell viability for HCT116 cells averaged ~83%, while RKO cells averaged 94%. For 62 μg/mL, HCT116 cells averaged 68% and RKO cells averaged 89% for. For concentrations above 100 μg/mL (125 and 250 μg/mL), cell survival for HCT116 was 13% and 7%, respectively. RKO cell viability for 125 and 250 μg/mL showed 20% and 0% cell viability. This means that ~125 μg/mL of PCPDTBSe in media is all one would need in order to initiate protein denaturation in-vitro.

EXAMPLE 2

NIR-Mediated Thermal Ablation of Bacteria Using Water Insoluble Conjugated Polymers Methods Two bacterial species with contrasting surface thickness and molecular composition were used to evaluate PEDOT NT hyperthermic interactions with the bacterial species. Bacterial strains were purchased from American Type Culture Collection (ATCC): gram positive *S. aureus*, ATCC 25923 and gram negative *E. coli*, ATCC 29055. The bacteria were grown overnight (tryptic soy broth the *S. aureus* and nutrient broth for *E. coli*), studied in their exponential phase of growth and suspended at a concentration of $10^8$ bacteria per ml for exposure to the nanoparticles. PEDOT NT were purchased from Sigma Aldrich. To aid in the aqueous solubility of the PEDOT NT, the PEDOT NT were suspended in an aqueous solution containing 1% Pluronic (F127) surfactant. PEDOT NT were added to the bacterial suspensions at a concentration of 0.1 mg/ml, and 300 μL aliquots of nanoparticle/bacteria solution were exposed to laser radiation. A Nd:YAG continuous wave laser with wavelength of 1064 nm and 3 W power was used to irradiate the bacterial suspensions, with and without nanotubes, for 30, 60 or 120 seconds. Nanoparticles were introduced to the bacterial suspensions immediately prior to laser exposure, and the total time of nanoparticle exposure was 15 minutes. Immediately following laser application, 100 μl of the nanoparticle/bacteria suspension was streaked onto agar (Columbia blood agar for *S. aureus* and nutrient agar for *E. coli*) plates and incubated for 24 hours at 37° C. in a humidified incubator. The total number of colony forming units (CFUs) was counted to determine the extent of bacterial kill. Each bacterial suspension was done in triplicate and triplicate agar plates were used for each experimental group.

Figure 9:
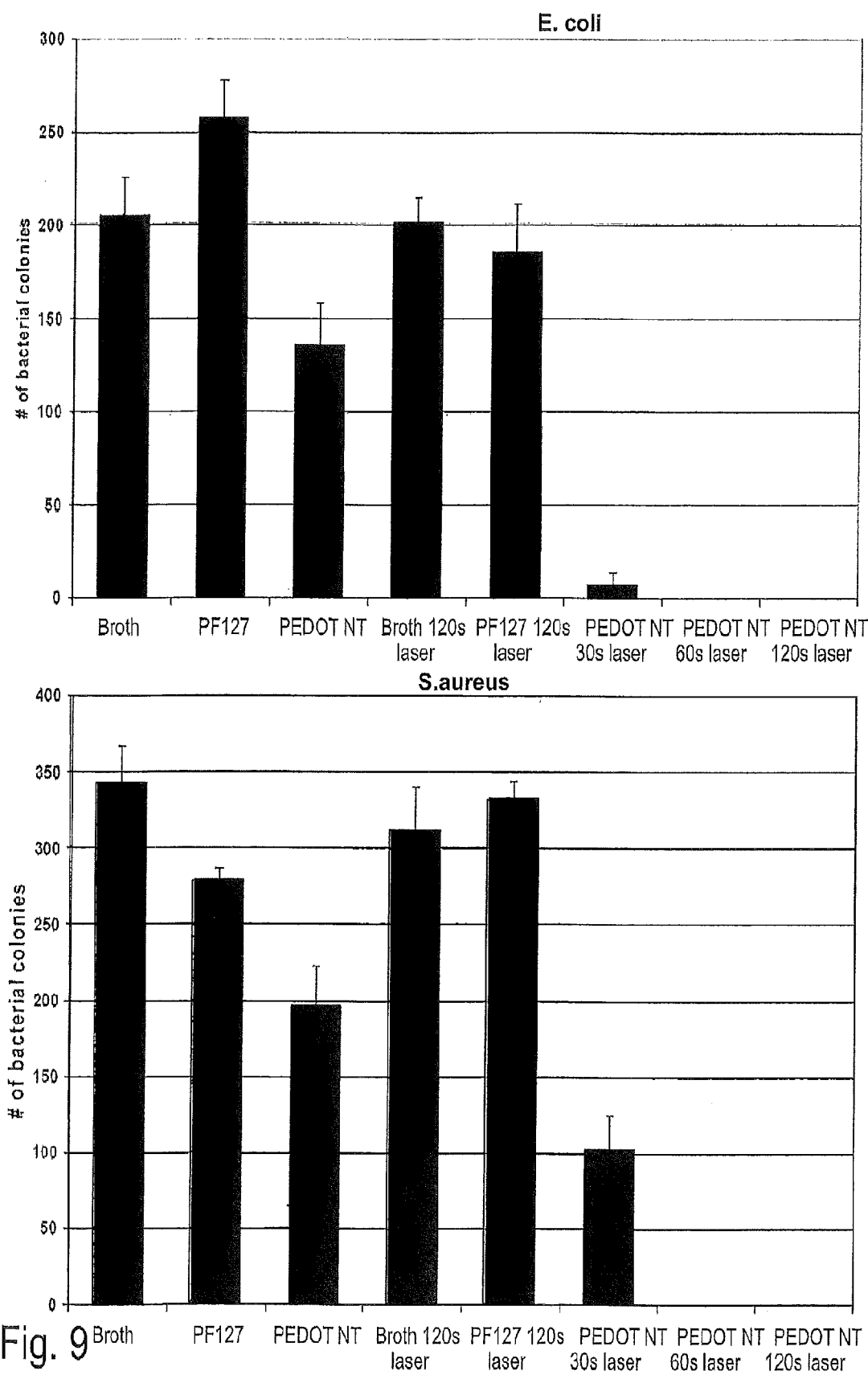
FIG. 9 illustrated PEDOT NT induced hyperthermia against two bacteria types according to one embodiment described herein.

Results of the laser exposure in the presence of the PEDOT NT compositions are provided in FIG. 9. As illustrated in FIG. 9, the PEDOT NT completely eradicated the both *S. aureus* and *E. coli* at irradiation times of 60 seconds or greater. Moreover, the PEDOT-NT demonstrated a greater killing effect for irradiation times less than 60 seconds.

EXAMPLE 3

NIR-Mediated Thermal Ablation of Cancer Cells Using Aqueous Solutions or Colloidal Compositions of Water Insoluble Conjugated Polymers Materials and Methods All reagents were purchased from common commercial sources and used without further purification unless otherwise noted. In addition, where relevant, all other materials were obtained and all measurement methods were carried out as described in Example 1, unless otherwise noted.

Figure 10:
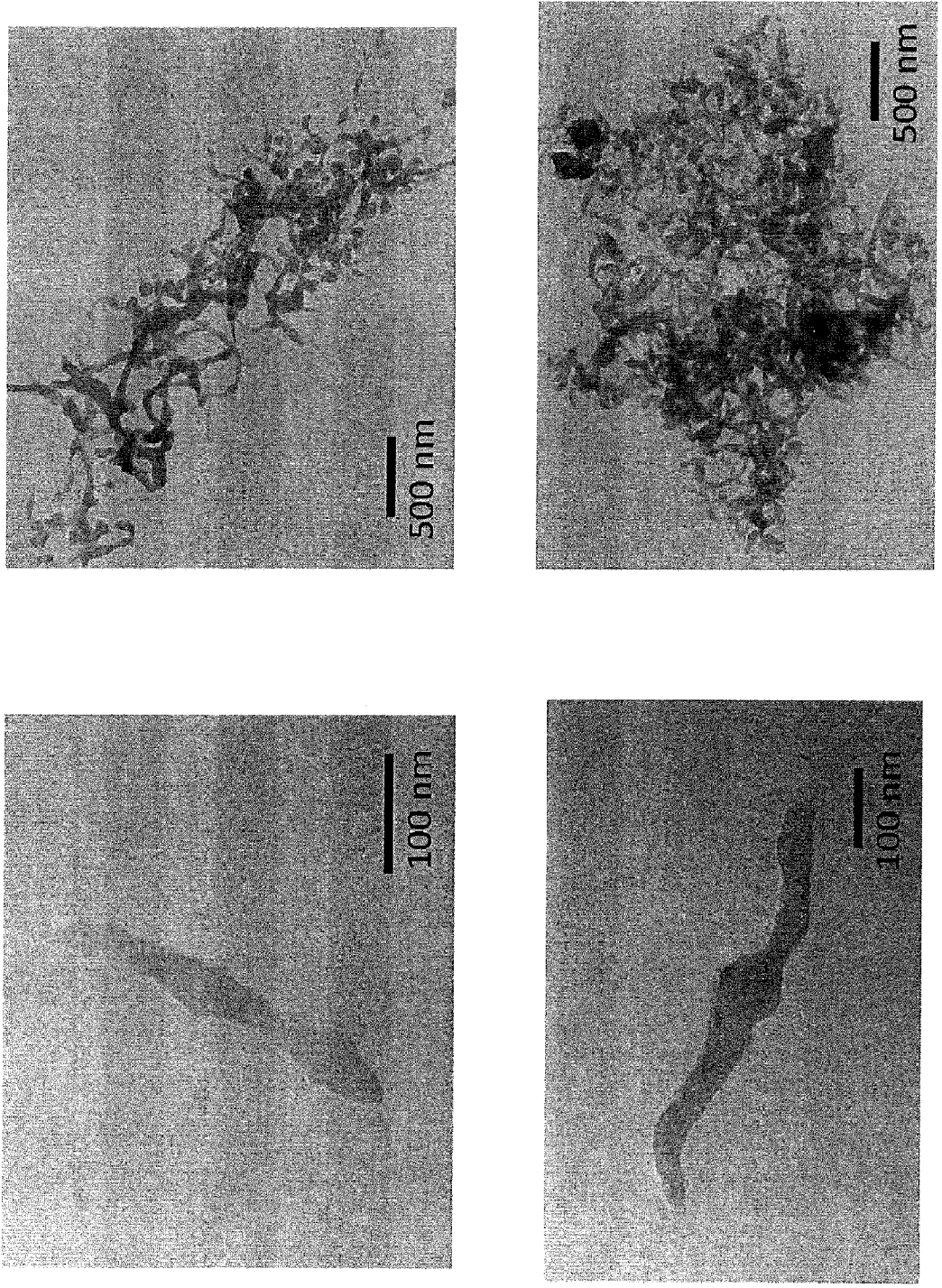
FIG. 10 illustrates TEM images of a solubilized water insoluble conjugated polymer according to one embodiment described herein.
Figure 11:
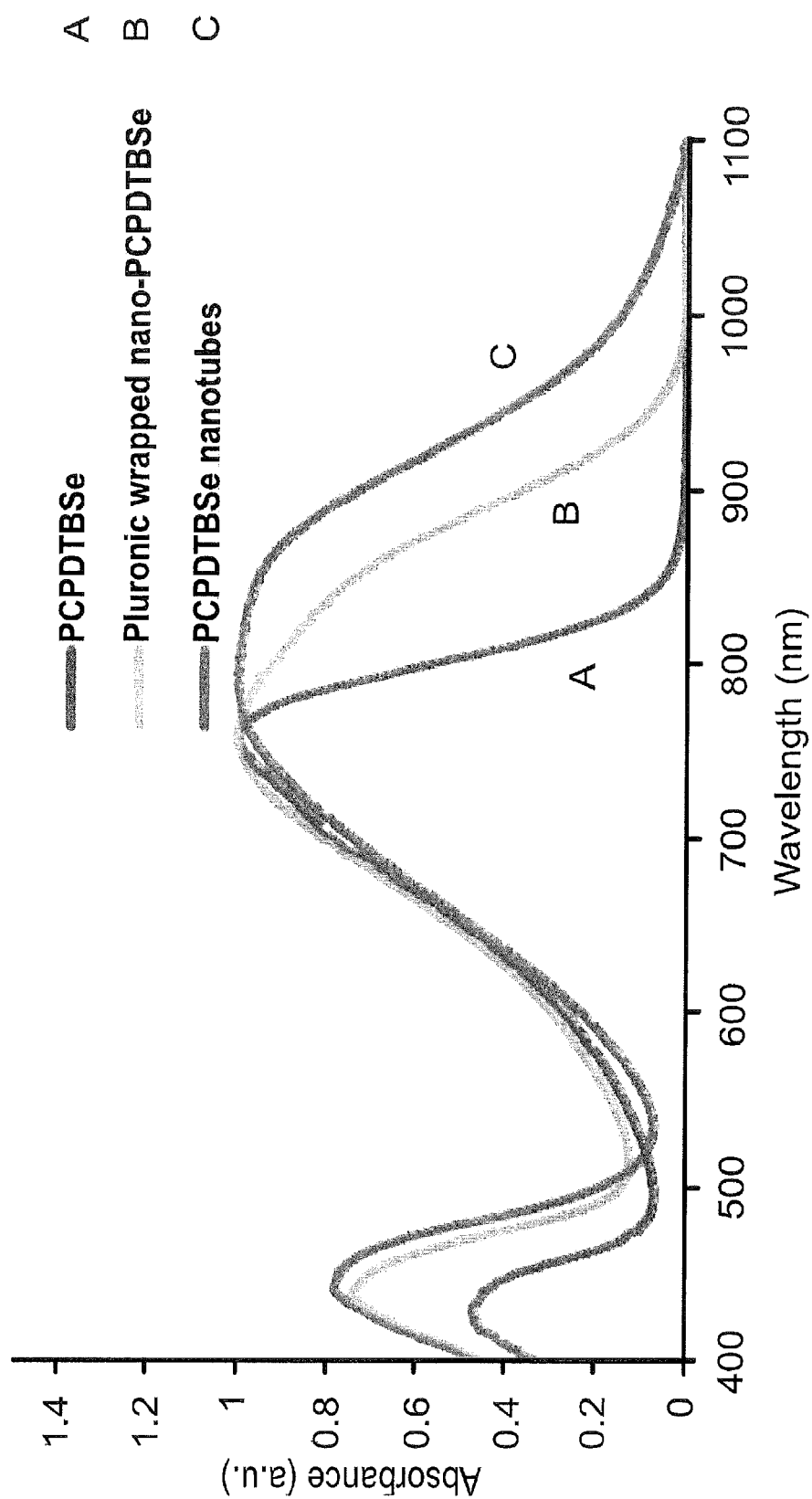
FIG. 11 illustrates absorbance values for a solubilized water insoluble conjugated polymer according to some embodiments described herein.

Formation of Aqueous Solutions or Colloidal Compositions of PCPDTBSe Nanotubes and Spherical Nanoparticles PCPDTBSe (5 mg) was dissolved in 2 mL of THF. This solution was rapidly injected into 8 mL of DI water containing Pluronic F127 (50 mg) under horn sonication. After 1 minute sonication, the resulting mixture was centrifuged for 15 minutes at 14,000 RPM to separate PCPDTBSe nanotubes from substantially spherical nanoparticles. FIG. 10 illustrates transmission electron microscope (TEM) images of the isolated nanotubes. The nanotubes exhibited widths or diameters of about 20 nm to 30 nm and lengths of about 200 nm to 600 nm. FIG. 11 illustrates absorbance spectra of PCPDTBSe nanotubes (Curve C), PCPDTBSe nanoparticles (Curve B) at least partially encapsulated by Pluronic F127, and PCPDTBSe polymer in non-nanomeric form (Curve A).

Cytotoxicity of PCPDTBSe Isotropic Nanoparticles and PCPDTBSe Nanotubes

Figure 12:
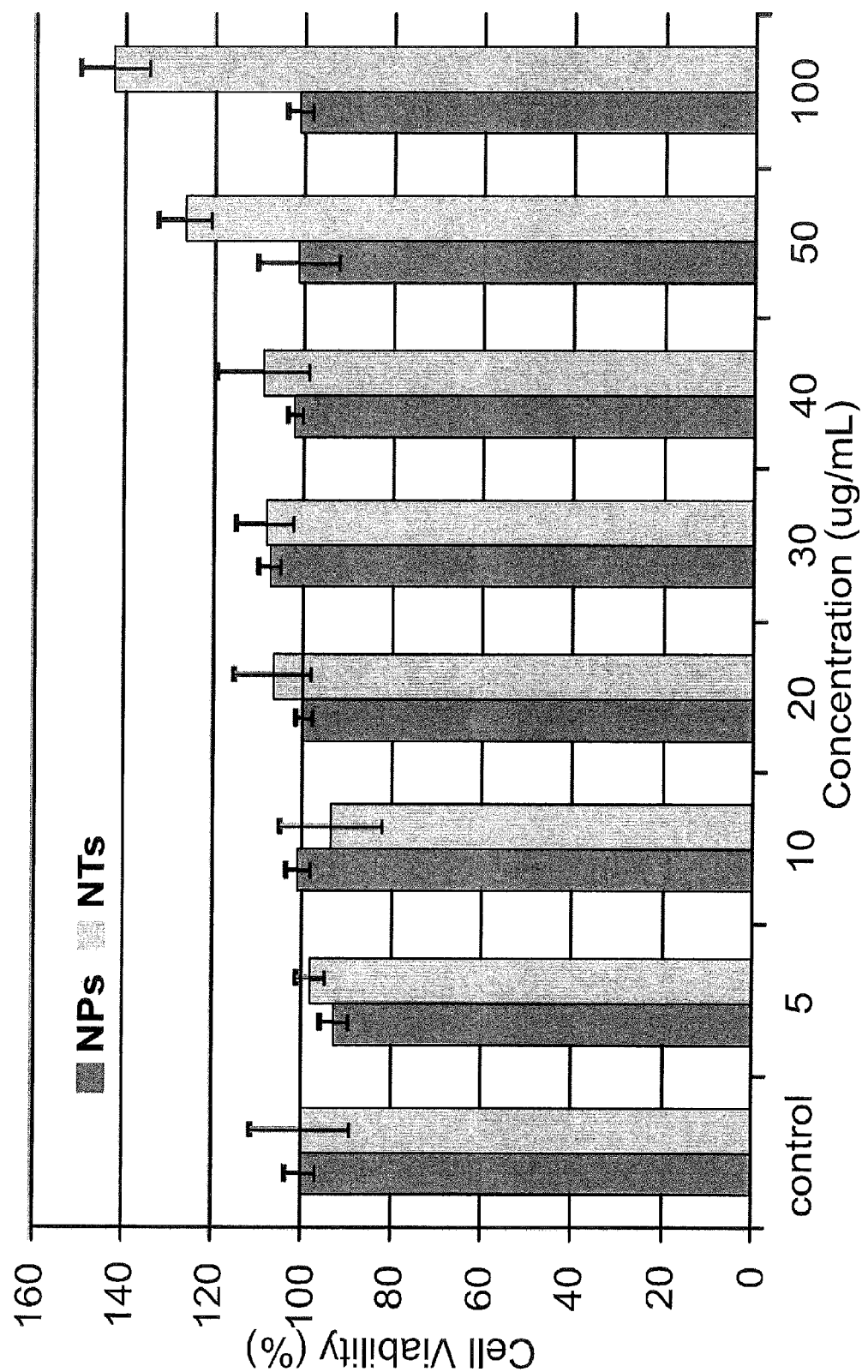
FIG. 12 illustrates results of a cytotoxicity screen of a solubilized water insoluble conjugated polymer according to some embodiments described herein.

A cytotoxicity study of the PCPDTBSe nanoparticles and nanotubes was carried out as described in Example 1, except luciferase CT 26 cells were used. In addition, the cells were incubated in the presence of nanoparticles and nanotubes for 24 hours without NIR irradiation at concentrations of 5, 10, 20, 30, 40, 50, and 100 µg/mL. Results were compared to a control well normalized to 100% cell viability. FIG. 12 illustrates the results. As illustrated in FIG. 12, the PCPDTBSe nanoparticles and nanotubes showed no significant toxicity towards the luciferase CT 26 cells at concentrations from 5-100 µg/mL.

Cell Viability Studies

Figure 13:
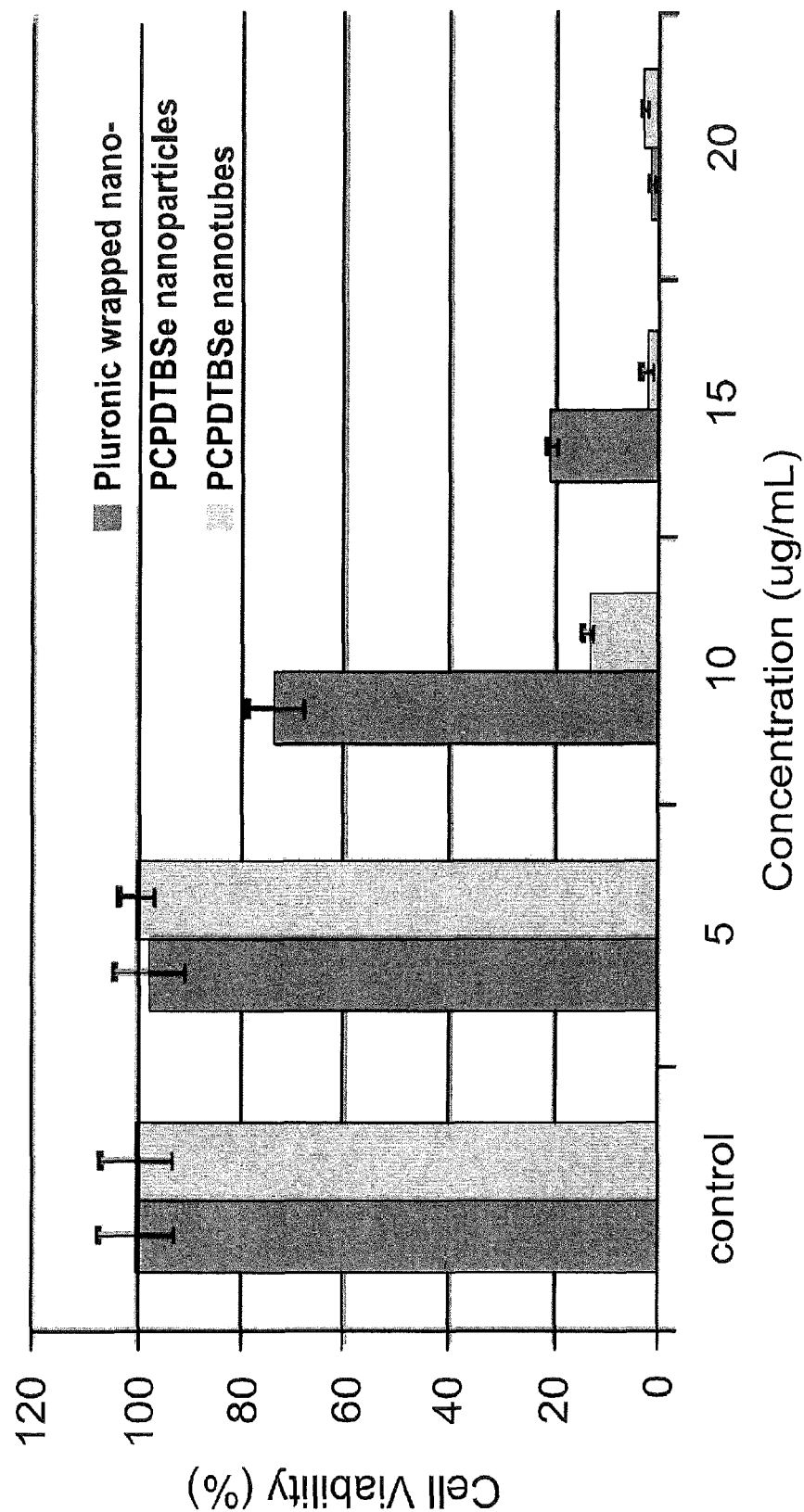
FIG. 13 illustrates results of thermally treating breast cancer cells by irradiation of an aqueous solution of a solubilized water insoluble conjugated polymer according to one embodiment described herein.

The MDA MB 231 breast cancer cell line was used in this study. When NIR radiation is applied to different concentrations of pluronic wrapped PCPDTBSe nanoparticles and nanotubes in aqueous media, the polymer generates heat which destroys the surrounding cancer cells. An 800 nm laser generating 3 W of power was irradiated onto aqueous solutions of PCPDTBSe isotropic nanoparticles and nanotubes in media containing MDA MB 231 cells for 1 minute at four different concentrations. The results are shown in FIG. 13. The control well was normalized to 100% viability, and error bars are shown as standard deviation of the mean (3 wells).

EXAMPLE 4

NIR-Mediated Thermal Ablation of Cancer Cells Using Aqueous Solutions or Colloidal Compositions of Water Insoluble Conjugated Polymers Materials and Methods All reagents were purchased from common commercial sources and used without further purification unless otherwise noted. In addition, where relevant, all other materials were obtained and all measurement methods were carried out as described in Example 1, unless otherwise noted.

Formation of Aqueous Solutions or Colloidal Compositions of PCPDTBSe Spherical Nanoparticles PCPDTBSe was dissolved in 2 mL of THF. This solution was rapidly injected into 8 mL of DI water containing carboxyl terminated polyethylene glycol phospholipid (PL-PEG-COOH) under horn sonication. After 2 minutes of horn sonication, the resulting mixture was centrifuged for 4 hours at 14,000 RPM and washed twice with DI water to provide PCPDTBSe nanoparticles wrapped or at least partially encapsulated by PL-PEG-COOH. Varying amounts of PCPDTBSe and PL-PEG-COOH were used in different syntheses, as shown in Table IV for Examples 4A-4E.

TABLE IV

| | Amounts of Reagents | | | | |
|---|---|---|---|---|---|
| Reagent | Ex. 4A | Ex. 4B | Ex. 4C | Ex. 4D | Ex. 4E |
| PCPDTBSe | 1 mg | 0.25 mg | 0.25 mg | 0.25 mg | 0.1 mg |
| PL-PEG | 1 mg | 0.9 mg | 1 mg | 2.25 mg | 2.25 mg |
| Excess of PL-PEG | 1x | 3.6x | 4x | 9x | 22.5x |

Figure 14:
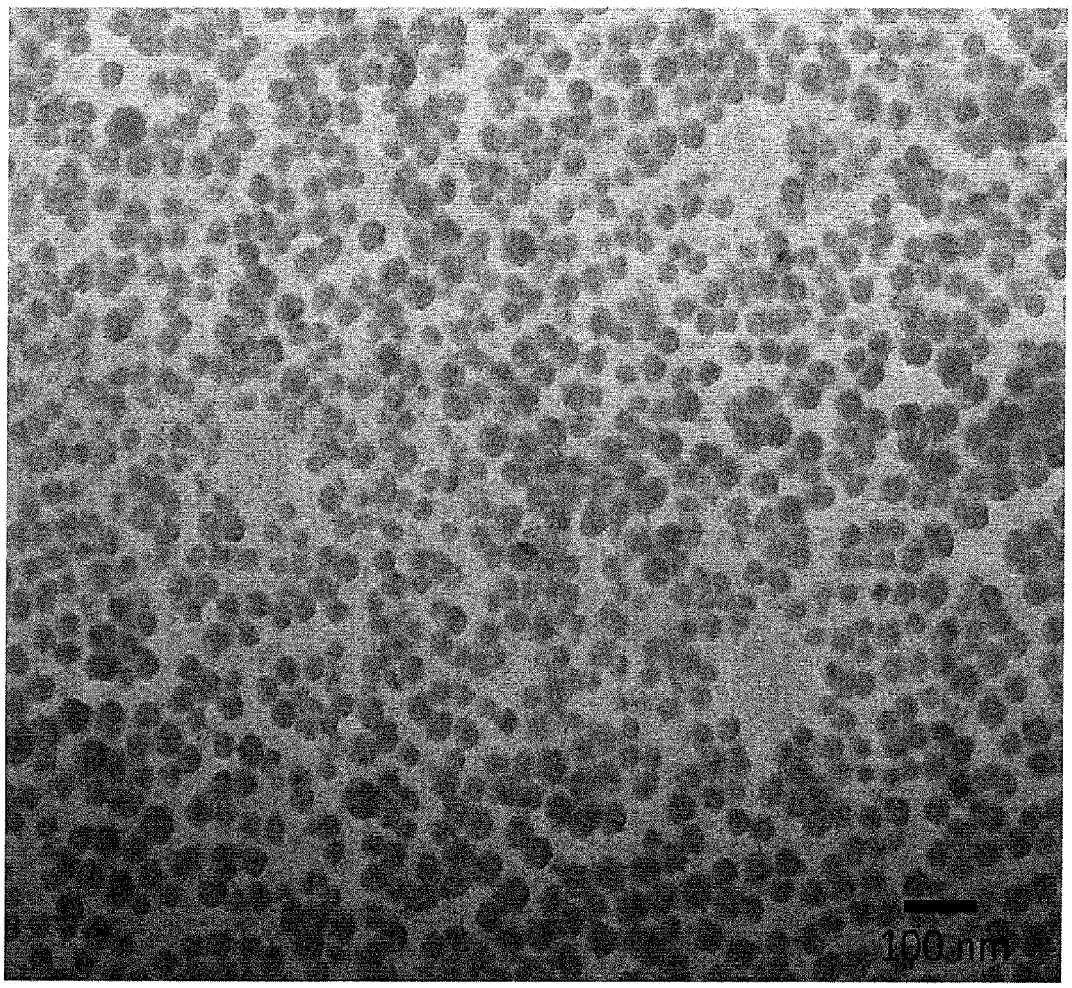
FIG. 14 illustrates a TEM image of a solubilized water insoluble conjugated polymer according to one embodiment described herein.
Figure 15:
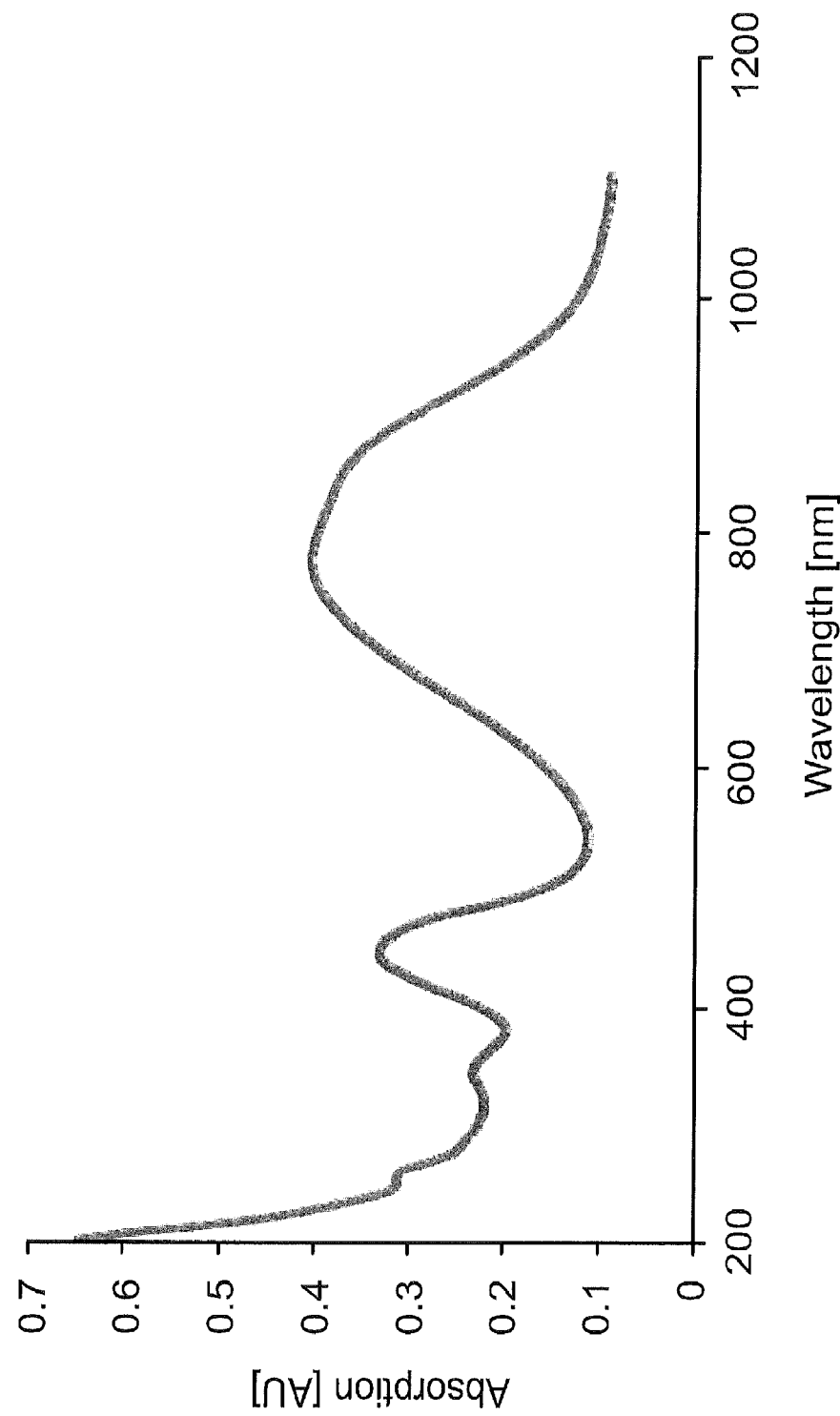
FIG. 15 illustrates an absorbance spectrum for a solubilized water insoluble conjugated polymer according to one embodiment described herein.
Figure 16:
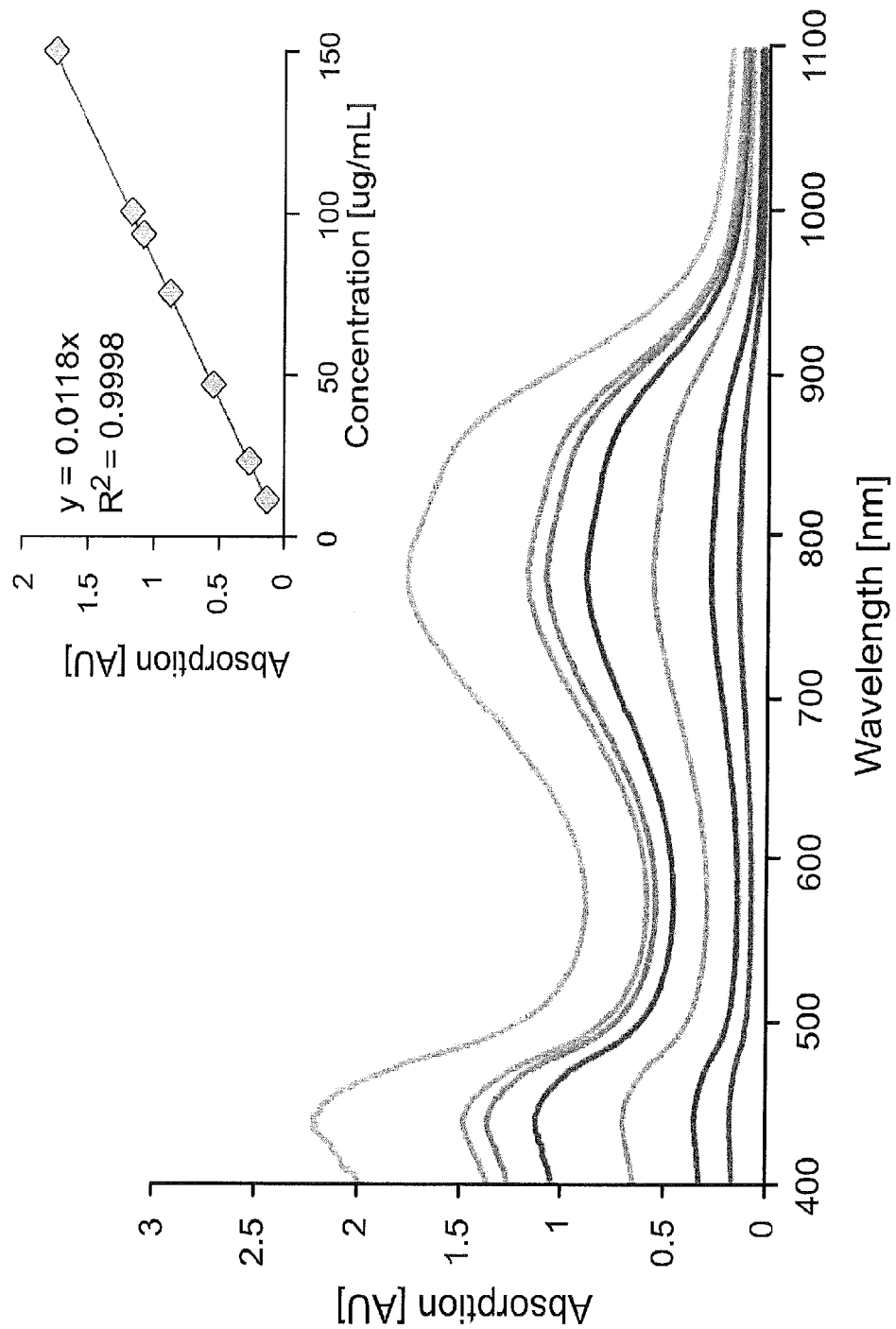
FIG. 16 illustrates aqueous solution concentrations and corresponding absorbance values for a solubilized water insoluble conjugated polymer according to one embodiment described herein.

FIG. 14 illustrates a transmission electron microscope (TEM) image of the isolated PCPDTBSe nanoparticles. FIG. 15 illustrates an absorbance spectrum of the PCPDTBSe nanoparticles. FIG. 16 illustrates a concentration-absorbance calibration curve for the PCPDTBSe nanoparticles. Dynamic light scattering analysis of the PCPDTBSe nanaoparticles provided a number average diameter of 20 (±5) nm. Zeta potential measurements of the PCPDTBSe nanoparticles provided a zeta potential value of −44.16 (+2.76).

NIR Heating of PCPDTBSe-PL-PEG-COOH Spherical Nanoparticles

Figure 17:
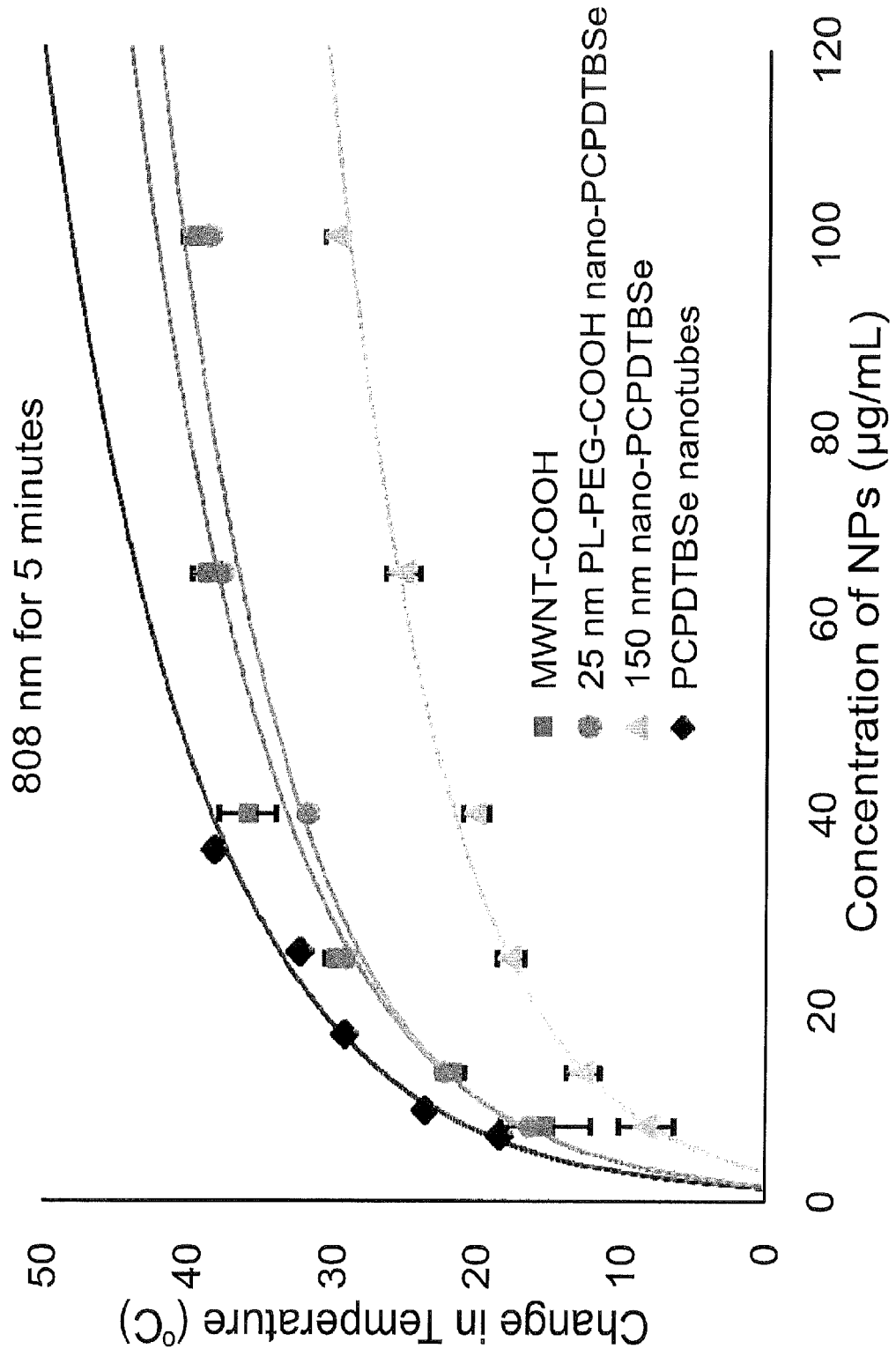
FIG. 17 provides a plot of the change in temperature versus concentration for various nanoparticle compositions.

In order to test the heating efficacy of the PCPDTBSe-PL-PEG-COOH nanoparticles, nanoparticles having an average size of 25 nm were compared to different concentrations of oxidized multi-walled carbon nanotubes (MWNT-COOH), isotropic PCPDTBSe nanoparticles of Example 3 having a size of 150 nm, and PCPDTBSe nanotubes of Example 3. All samples were tested in McCoys 5A cell medium and illuminated with an 808 nm laser (0.5 W) for five minutes. A plot of the change in temperature vs. concentration for the various samples is shown in FIG. 17. As illustrated in FIG. 17, PCPDTDSe nanotubes demonstrated greater heating than the MWNT-COOH.

Cytotoxicity of PCPDTBSe-PL-PEG-COOH Nanoparticles

Figure 18:
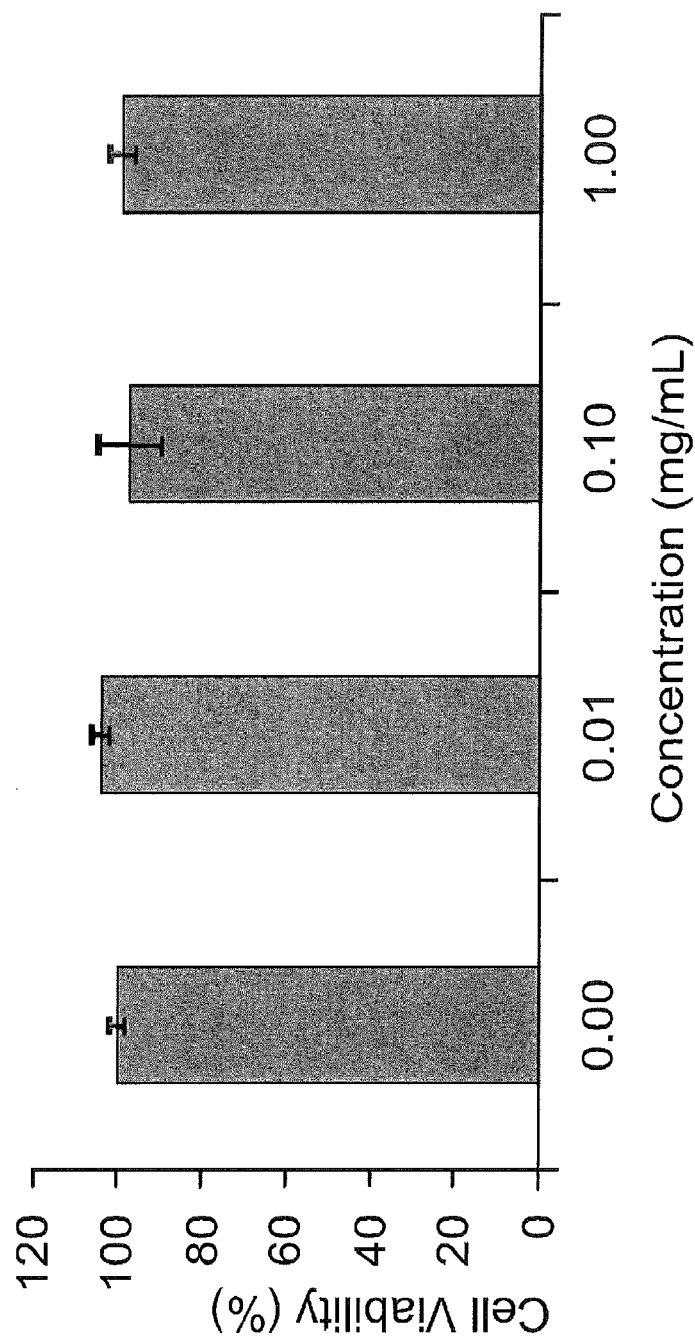
FIG. 18 illustrates results of a cytotoxicity screen of a solubilized water insoluble conjugated polymer according to some embodiments described herein.
Figure 19:
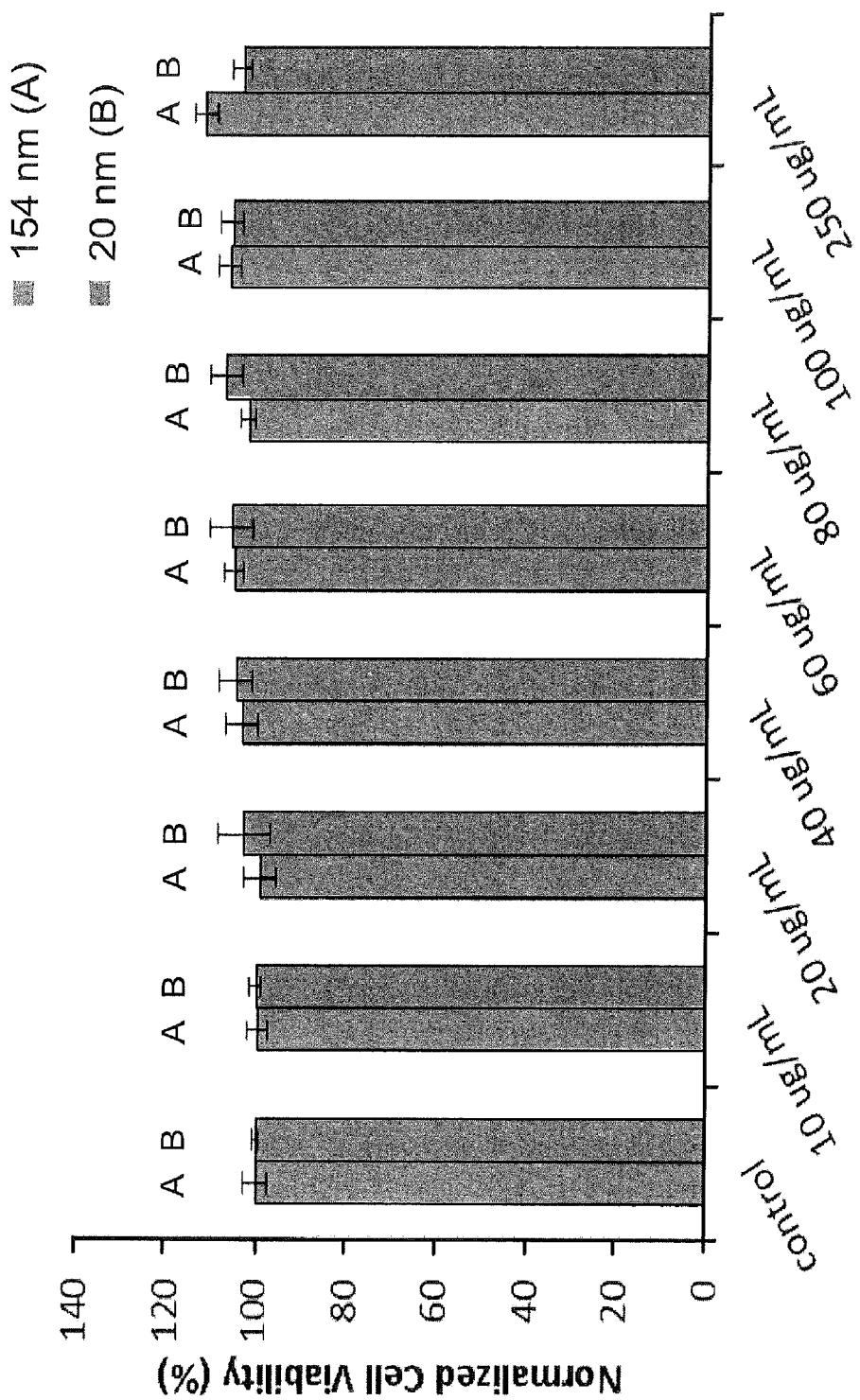
FIG. 19 illustrates results of a cytotoxicity screen of a water insoluble conjugated polymer according to some embodiments described herein.

Cytotoxicity studies of PCPDTBSe-PL-PEG-COOH nanoparticles having an average size of 20 nm were carried out using RKO and CT 26 colorectal cancer cells. The cells were added to the top of a layer of nanoparticles providing by evaporating the solvent from a dispersion of the nanoparticles in ethanol. Cells were incubated in the presence of nanoparticles for 24 hours without NIR irradiation at concentrations of 0.01, 0.10, and 1.00 mg/mL (for RKO cells) and 10, 20, 40, 60, 80, 100, and 250 µg/mL (for CT 26 cells). Results were compared to control wells normalized to 100% cell viability. In addition, for the studies using CT 26 cells, results for the PCPDTBSe-PL-PEG-COOH nanoparticles were compared to results for PCPDTBSe nanoparticles according to Example 1 and having an average size of 154 nm. FIG. 18 illustrates the results for the RKO cells. FIG. 19 illustrates the results for the CT 26 cells (154 nm particles of Example 1 are marked as "A" on the left, and 20 nm particles are marked as "B" on the right). As illustrated in FIGS. 18 and 19, the PCPDTBSe-PL-PEG-COOH nanoparticles showed no significant toxicity towards the RKO and CT 26 cells at the concentrations tested.

Cell Viability Studies

Figure 20:
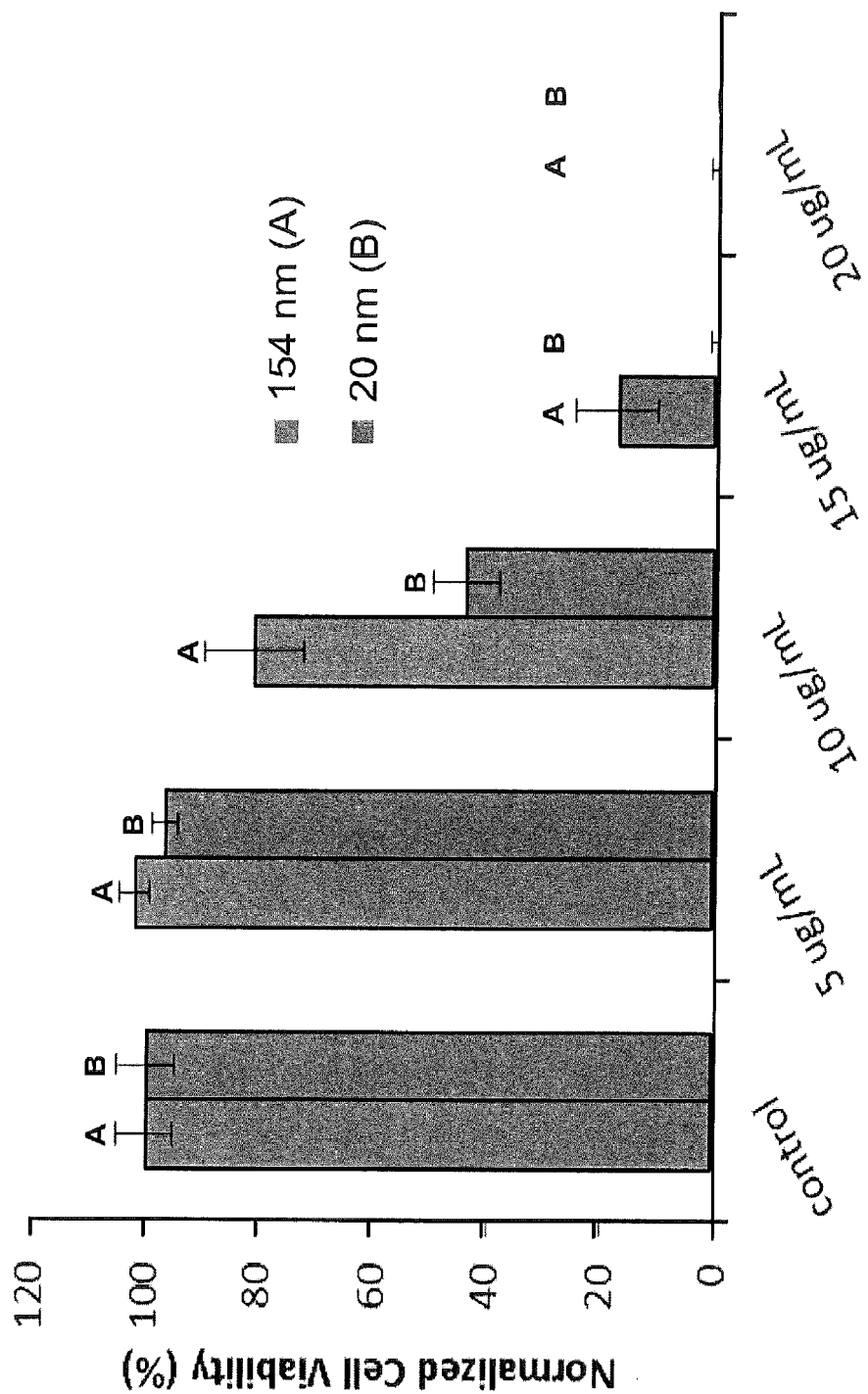
FIG. 20 illustrates results of thermally treating colorectal cancer cells by irradiation of an aqueous solution of a solubilized water insoluble conjugated polymer according to some embodiments described herein.

The CT 26 colorectal cancer cell line was used in this study. When NIR radiation is applied to different concentrations and sizes of PCPDTBSe nanoparticles in aqueous media, the polymer generates heat which destroys the surrounding cancer cells. An 800 nm laser generating 3 W of power was irradiated onto aqueous solutions of PCPDTBSe isotropic nanoparticles in media containing CT 26 cells for 60 seconds (for a total irradiation of 180 J/cm$^2$) at four different concentrations (5, 10, 15, and 20 µg/mL). Nanoparticles having an average size of 154 nm and nanoparticles having an average size of 20 nm were used. The results are shown in FIG. 20 (154 nm particles are marked as "A," and 20 nm particles are marked as "B"). The control wells were normalized to 100% viability, and error bars are shown as standard deviation of the mean (3 wells).

EXAMPLE 5

Aqueous Solutions or Colloidal Compositions of Water Insoluble Conjugated Polymers Materials and Methods All reagents were purchased from common commercial sources and used without further purification unless otherwise noted. In addition, where relevant, all other materials were obtained and all measurement methods were carried out as described in Example 1, unless otherwise noted, Formation of Aqueous Solutions or Colloidal Compositions of PCPDTBSe Nanoparticles Comprising a Light Emitting Species PCPDTBSe nanoparticles comprising FITC were prepared as described for the PCPDTBSe-PL-PEG-COOH nanoparticles in Example 4, except PL-PEG-COOH was replaced with a 1:10 mixture (by weight) of PL-PEG-COOH and PL-PEG-FITC (a PL-PEG conjugated to FITC).

Figure 21:
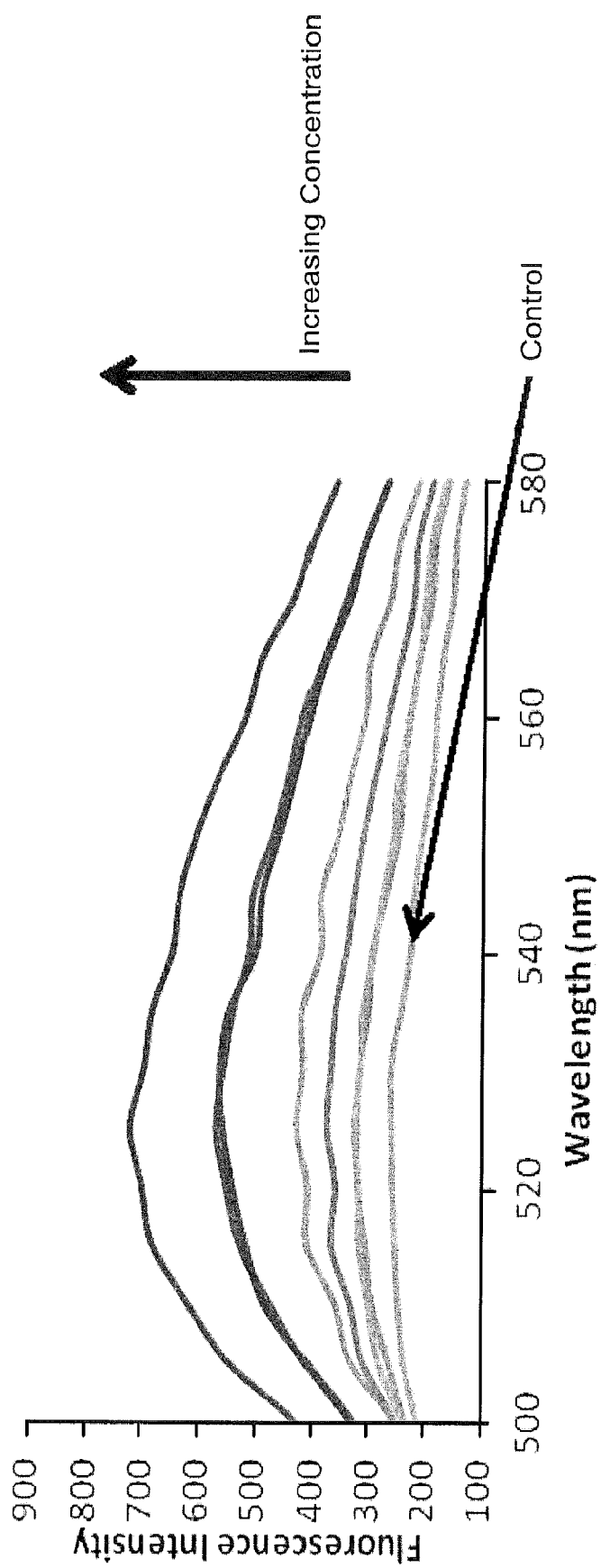
FIG. 21 illustrates fluorescence values for a solubilized water insoluble conjugated polymer according to some embodiments described herein.

As shown in FIG. 21, fluorescence of the resulting nanoparticles was observed when the nanoparticles were excited at 454 nm and 490 nm. The fluorescence profile exhibited a peak at 525 nm.

Various embodiments of the invention have been described in fulfillment of the various objectives of the invention. It should be recognized that these embodiments are merely illustrative of the present invention. Numerous modifications and adaptations thereof will be readily apparent to those of skill in the art without departing from the spirit and scope of the invention.

That which is claimed is:

1. A composition comprising:
an aqueous medium; and
particles of at least one water insoluble conjugated copolymer dispersed in the aqueous medium, the particles having a band gap ranging from about 1.1 eV to about 1.8 eV,
wherein the water insoluble conjugated copolymer has a donor-acceptor architecture comprising a donor monomeric species (D) and an acceptor monomeric species (A),
wherein the donor monomeric species is a fused dithiophene of the formula

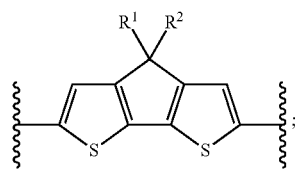

wherein the acceptor monomeric species is a benzodiazole of the formula

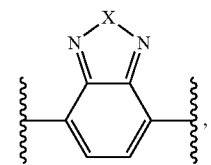

wherein $R^1$ and $R^2$ are selected from the group consisting of hydrogen, alkyl, alkenyl, aryl, heteroaryl, O-alkyl, O-alkenyl, and O-aryl, and
wherein X is selected from the group consisting of oxygen, nitrogen, sulfur and selenium.

2. The composition of claim 1, wherein the particles of the water insoluble conjugated copolymer are nanotubes or other anisotropically shaped nanoparticles.

3. The composition of claim 2, wherein the nanotubes or other anisotropically shaped nanoparticles have a length ranging from 1 nm to 10 µm.

4. The composition of claim 2, wherein the nanotubes or other anisotropically shaped nanoparticles have a length ranging from 200 nm to 600 nm.

5. The composition of claim 2, wherein the nanotubes or other anisotropically shaped nanoparticles have a diameter ranging from 1 nm to 500 nm.

6. The composition of claim 2, wherein the nanotubes or other anisotropically shaped nanoparticles have a diameter ranging from 15 nm to 300 nm.

7. The composition of claim 1, wherein the particles of the water insoluble conjugated copolymer are dispersed in the aqueous medium to provide a colloid.

8. The composition of claim 7, wherein the particles of the water insoluble conjugated copolymer are at least partially encapsulated by a dispersing agent.

9. The composition of claim 8, wherein the dispersing agent comprises a surfactant.

10. The composition of claim 9, wherein the surfactant is a non-ionic polyol.

11. The composition of claim 8, wherein the dispersing agent is a phospholipid.

12. The composition of claim 1, wherein the particles are conjugated or attached to one or more targeting agents, the targeting agents comprising an antibody, a chemokine receptor, and/or a targeting ligand.

13. The composition of claim 1, wherein the water insoluble conjugated copolymer is present in the aqueous medium at a concentration of 1 ng/ml to 100 mg/ml.

14. The composition of claim 1, wherein the water insoluble conjugated copolymer is present in the aqueous medium at a concentration of 1 μg/ml to 120 μg/ml.

15. The composition of claim 1, wherein the water insoluble conjugated copolymer is present in the aqueous medium at a concentration of 5 μg/ml to 30μg/ml.

16. The composition of claim 1, wherein the water insoluble conjugated copolymer is present in the aqueous medium at a concentration of 15 μg/ml to 25 μg/ml.

17. The composition of claim 1, wherein X is selenium.

18. The composition of claim 1, wherein X is nitrogen.

19. The composition of claim 1, wherein particles of the at least one water insoluble conjugated copolymer are not dispersed by surfactant.

* * * * *